US009103823B2

(12) United States Patent
Elsemore et al.

(10) Patent No.: US 9,103,823 B2
(45) Date of Patent: *Aug. 11, 2015

(54) METHODS, DEVICES, KITS AND COMPOSITIONS FOR DETECTING ROUNDWORM

(71) Applicants: IDEXX Laboratories, Inc., Westbrook, ME (US); Divergence, Inc., St. Louis, MO (US)

(72) Inventors: David Allen Elsemore, South Portland, ME (US); Laurie A. Flynn, Raymond, ME (US); Jinming Geng, Scarborough, ME (US); Michael Crawford, St. Louis, MO (US)

(73) Assignees: Idexx Laboratories, Inc., Westbrook, ME (US); Divergence, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/045,077

(22) Filed: Oct. 3, 2013

(65) Prior Publication Data
US 2014/0170684 A1 Jun. 19, 2014

Related U.S. Application Data

(62) Division of application No. 12/467,808, filed on May 18, 2009, now Pat. No. 8,580,518.

(60) Provisional application No. 61/128,099, filed on May 19, 2008.

(51) Int. Cl.
*C07K 16/18* (2006.01)
*G01N 33/543* (2006.01)
*C07K 14/435* (2006.01)
*C12Q 1/68* (2006.01)
*G01N 33/53* (2006.01)

(52) U.S. Cl.
CPC .......... *G01N 33/543* (2013.01); *C07K 14/4354* (2013.01); *C07K 16/18* (2013.01); *C12Q 1/6888* (2013.01); *G01N 33/5308* (2013.10)

(58) Field of Classification Search
USPC ........... 435/7.1, 4, 7.22, 7.92, 975; 530/387.1
See application file for complete search history.

(56) References Cited

U.S. PATENT DOCUMENTS

| 4,322,495 | A | 3/1982 | Kato |
|---|---|---|---|
| 4,756,908 | A | 7/1988 | Lew |
| 4,789,631 | A | 12/1988 | Maggio |
| 4,839,275 | A | 6/1989 | Weil |
| 4,978,504 | A | 12/1990 | Nason |
| 5,078,968 | A | 1/1992 | Nason |
| 5,238,649 | A | 8/1993 | Nason |
| 5,266,266 | A | 11/1993 | Nason |
| 5,726,010 | A | 3/1998 | Clark |
| 5,753,787 | A | 5/1998 | Hawdon et al. |
| 5,843,706 | A | 12/1998 | Cobon et al. |
| 5,882,943 | A | 3/1999 | Aldeen |
| 6,057,166 | A | 5/2000 | Childs et al. |
| 6,391,569 | B1 | 5/2002 | Grieve et al. |
| 6,596,502 | B2 | 7/2003 | Lee |
| 6,824,975 | B2 | 11/2004 | Hubscher et al. |
| 6,872,808 | B1 | 3/2005 | Vlasuk et al. |
| 7,303,752 | B2 | 12/2007 | Hotez et al. |
| 7,736,660 | B2 | 6/2010 | Elsemore et al. |
| 7,781,170 | B2 | 8/2010 | Tonelli et al. |
| 7,951,547 | B2 | 5/2011 | Elsemore et al. |
| 7,993,862 | B2 | 8/2011 | Elsemore et al. |
| 8,097,261 | B2 | 1/2012 | Elsemore et al. |
| 2002/0132270 | A1 | 9/2002 | Lee |
| 2003/0129680 | A1 | 7/2003 | O'Connor |
| 2004/0014087 | A1 | 1/2004 | Hodgson et al. |
| 2004/0214244 | A1 | 10/2004 | Tonelli |
| 2005/0042232 | A1 | 2/2005 | Hotez et al. |
| 2006/0129327 | A1 | 6/2006 | Kim et al. |
| 2006/0198844 | A1 | 9/2006 | Langenfeld |
| 2007/0053920 | A1 | 3/2007 | Heath et al. |
| 2007/0178606 | A1 | 8/2007 | Imoarai et al. |
| 2008/0033148 | A1 | 2/2008 | Xu et al. |
| 2008/0108793 | A1 | 5/2008 | Berman et al. |

(Continued)

FOREIGN PATENT DOCUMENTS

| JP | 2007121270 | 5/2007 |
|---|---|---|
| WO | WO 98/12563 | 3/1998 |

(Continued)

OTHER PUBLICATIONS

Hawley, J.H. et al., "Proteinase Inhibitors in Ascarida," Parasitology Today, vol. 10, Issue 8, pp. 308-318 (1994).
Wattanakulpanich et al., "Application of *Toxocara canis* excretory-secretory antigens and IgG subclass antibodies (IgG1-4) in serodiagnostic assays of human toxocariasis," Acta Tropica, vol. 106, pp. 90-95 (2008).
Kennedy et al., "Antigenic relationships between the surface-exposed, secreted and somatic materials of the nematode parasites *Ascaris lumbricoides*, *Ascaris suum*, and *Toxocara canis*," Clin. Exp. Immunol., vol. 75, No. 3, pp. 493-500 (Mar. 1989).

(Continued)

*Primary Examiner* — Jennifer Graser
(74) *Attorney, Agent, or Firm* — McDonnell Boehnen Hulbert & Berghoff LLP

(57) ABSTRACT

Methods, devices, kits and compositions for detecting the presence or absence of roundworm in a fecal sample are disclosed herein. The methods, devices, kits and compositions of the present invention may be used to confirm the presence or absence of roundworm in a fecal sample from a mammal that may also be infected with one or more of hookworm, whipworm, and heartworm. Confirmation of the presence or absence of roundworm in the mammal may be made, for example, for the purpose of selecting an optimal course of treating the mammal and/or for the purpose of determining whether the mammal has been rid of the infection after treatment has been initiated.

11 Claims, 28 Drawing Sheets

(56) References Cited

U.S. PATENT DOCUMENTS

| | | | |
|---|---|---|---|
| 2008/0311557 A1 | 12/2008 | Elsemore et al. |
| 2008/0311600 A1 | 12/2008 | Elsemore et al. |
| 2009/0286227 A1 | 11/2009 | Elsemore et al. |
| 2009/0286228 A1 | 11/2009 | Elsemore et al. |
| 2009/0286229 A1 | 11/2009 | Elsemore et al. |
| 2009/0286230 A1 | 11/2009 | Elsemore et al. |
| 2009/0286231 A1 | 11/2009 | Elsemore et al. |
| 2010/0151500 A1 | 6/2010 | Elsemore et al. |
| 2011/0086340 A1 | 4/2011 | Elsemore et al. |

FOREIGN PATENT DOCUMENTS

| | | |
|---|---|---|
| WO | WO 02/075313 | 9/2002 |
| WO | WO 03/032917 | 4/2003 |
| WO | 2004064864 | 8/2004 |
| WO | WO 2004/097412 | 11/2004 |
| WO | WO 2006/135799 | 12/2006 |
| WO | 2008156648 | 12/2008 |
| WO | WO 2008/156650 | 12/2008 |
| WO | 2009143079 | 11/2009 |
| WO | WO 2009/143080 | 11/2009 |
| WO | WO 2009/143083 | 11/2009 |
| WO | 2011063009 | 5/2011 |

OTHER PUBLICATIONS

Matsumura et al., "Detection of circulating toxocaral antigens in dogs by sandwich enzyme-immunoassay," Immunology, vol. 51, pp. 609-613 (1984).

Bowman, D.D. et al., "*Toxocara canis*: Monoclonal Antibodies to Larval Excretory-Secretory Antigens that Bind with Genus and Species Specificity to the Cuticular Surface of Infective Larvae," Experimental Parasitology, vol. 64, pp. 458-465 (Dec. 1987).

Robertson, B.D. et al., "Detection of circulating parasite antigen and specific antibody in *Toxocara canis* infections," Clin. Exp. Immunol., vol. 74, pp. 236-241 (1988).

Iddawela et al., "Characterization of a *Toxocara canis* species-specific excretory-secretory antigen (TcES-57) and development of a double sandwich ELISA for diagnosis of visceral larva migrans," Korean Journal of Parasitology, vol. 45, No. 1, pp. 19-26 (Mar. 2007).

Alcantara-Neves et al., "An improved method to obtain antigen-excreting *Toxocara canis* larvae," Experimental Parasitology, vol. 199, pp. 349-351 (2008).

Babin, et al., "The Isoinhibitors of Chymotrypsin/Elastase from *Ascaris lumbricoides*: The Primary Structure", Archives of Biochemistry and Biophysics, vol. 232, No. 1, pp. 143-161, (1984).

Cappello, et al., "*Ancylostoma caninum* anticoagulant peptide: A hookworm-derived inhibitor of human coagulation factor Xa", Proc. Natl. Acad. Sci., vol. 92, pp. 6152-1656, (1995).

Ford, et al., "Characterization of a Novel Filarial Serine Protease Inhibitor, Ov-SPI-1, from *Onchocerca volvulus*, with Potential Multifunctional Roles during Development of the Parasite", J. of Biol. Chem., vol. 280, No. 49, pp. 40845-40856, (2005).

Fraefel, et al., "The amino acid sequence of a trypsin inhibitor isolated from *Ascaris* (*Ascaris lumbricoides* var. suum)", Biochim. Biophys. Acta, vol. 154, pp. 615-617, (1968).

Goodman, et al., "Isolation of the Trypsin Inhibitors in *Ascaris lumbricoides* var. suum Using Affinity Chromatography", Analytical Biochemistry, vol. 120, pp. 387-393 (1982).

Grasberger, et al., "High-resolution structure of *Ascaris* trypsin inhibitor in solution: direct evidence for a pH-induced conformational transition in the reactive site", Structure, vol. 2, No. 7, pp. 669-678, (1994).

Gronenborn et al., "Sequential resonance assignment and secondary structure determination of the *Ascaris trypsin* inhibitor, a member of a novel class of proteinase inhibitors", Biochemistry, vol. 29, No. 1, pp. 183-189, (1990).

Harrison, et al., "Molecular Characterization of *Ancylostoma* Inhibitors of Coagulation Factor Xa", J. of Biol. Chem., vol. 277, No. 8, pp. 6223-6229, (2002).

Hawley, et al., "*Ascaris suum*: Are Trypsin Inhibitors Involved in Species Specificity of Ascarid Nematodes?", Experimental Parasitology, vol. 75, pp. 112-118 (1992).

Huang, et al., "The molecular structure of the complex of *Ascaris* chymotrypsin/elastase inhibitor with porcine elastase", Structure, vol. 2, No. 7, pp. 679-689, (1994).

Lu, et al., "*Anisakis simplex*: Mutational Bursts in the Reactive Site Centers of Serine Protease Inhibitors from an Ascarid Nematode", Experimental Parasitology, vol. 89, pp. 257-261, (1998).

Martzen, et al., "*Ascaris suum*: Localization by Immunochemical and Fluorescent Probes of Host Proteases and Parasite Proteinase Inhibitors in Cross-sections", Experimental Parasitology, vol. 60, pp. 139-149, (1985).

Nguyen, et al., "Expression and characterization of elastase inhibitors from the ascarid nematodes *Anisakis simplex* and *Ascaris suum*", Mol. Biochem. Parasitology, vol. 102, pp. 79-89, (1999).

Peanasky, et al., "The Isoinhibitors of Chymotrypsin/Elastase from *Ascaris lumbricoides*: Isolation by Affinity Chromatography and Association with the Enzymes", Archives of Biochemistry and Biophysics, vol. 232, No. 1, pp. 127-134, (1984).

Rhoads, et al., "*Trichuris suis*: A Secretory Serine Protease Inhibitor", Experimental Parasitology, vol. 94, pp. 1-7, (2000).

Rhoads, et al., "*Trichuris suis*: A Secretory Chymotrypsin/Elastase Inhibitor with Potential as an Immunomodulator", Experimental Parasitology, vol. 95, pp. 36-44, (2000).

Stanssens, et al., "Anticoagulant repertoire of the hookworm *Ancylostoma canium*", Proc. Natl. Acad. Sci., vol. 93, pp. 2149-2154, (1996).

Uniprot Submission P07851. Aug. 1988. [Retrieved from the internet Dec. 13, 2009: URL:http://www.uniprot.org/uniprot/P07851.] in entirety.

Uniprot Submission P91811. May 1997 [Retrieved from the internet Nov. 7, 2009: [URL:http://www.uniprot.org/uniprot/P91811].

Uniprot Submission O44397. Jun. 1988 [Retrieved from the internet Nov. 11, 2009: [<URL:http://www.uniport.org/uniport/O44397>].

Ambler, et al., "Biological Techniques for Studying the Allergenic Components of Nematodes. I. Detection of Allergenic Components in *Ascaris suum* Extracts", J. Immunol. Methods, vol. 1, No. 4, pp. 317-327, (1972).

Britton, et al., "Extensive diversity in repeat unit sequences of the cDNA encoding the polyprotein antigen/allergen from the bovine lungworm *Dictyocaulus viviparous*", Mol. Biochem. Parasitol. vol. 72, Nos. 1-2, pp. 77-88, (1995).

Christie, et al., "The ABA-1 allergen of the nematode *Ascaris suum*: epitope stability, mass spectrometry, and N-terminal sequence comparison with its homologue in *Toxocara canis*", Clin. Exp. Immunol., vol. 92, pp. 125-132, (1993).

Kennedy, "Stage-specific secreted antigens of the parasitic larval stages of the nematode *Ascaris*" Immunology, vol. 58, No. 3, pp. 515-422, (1986).

McGibbon, et al., "Identification of the major *Ascaris* allergen and its purification to homogeneity by high-performance liquid chromatography", Mol. Biochem. Parasitol., vol. 39, No. 2, pp. 163-171, (1990).

Meenan, et al., "Resonance assignment of ABa-1A, from *Ascaris suum* nematode polyprotein allergen", J. Biomol. NMR, vol. 32, No. 2 p. 176, (2005).

Poole, et al., "Cloning of a cuticular antigen that contains multiple tandem repeats from the filarial parasite *Dirofilaria immitis*", Proc. Natl. Acad. Sci. USA, vol. 89, No. 13, pp. 5986-5990, (1992).

Solovyova, et al., "The polyprotein and FAR lipid binding proteins of nematodes: shape and monomer/dimer states in ligand-free and bound forms", Eur. Biophys. J., vol. 32, No. 5, pp. 465-476, (2003).

Spence, et al., "A cDNA encoding repeating units of the ABA-1 allergen of *Ascaris*", Mol. Biochem. Parasitol. vol. 57, pp. 339-343, (1993).

The C. elegans consortium, et al., "Genome Sequence of the Nematode *C. elegans*: A Platform for Investigating Biology", Science, vol. 282, pp. 2012-2018, (1998).

Tweedie, et al., "*Brugia pahangi* and *Brugia malayi*: a surface-associated glycoprotein (gp15/400) is composed of multiple tandemly repeated units and processed from a 400-kDa precursor", Exp. Parasitol., vol. 76, No. 2, pp. 156-164, (1993).

(56) References Cited

OTHER PUBLICATIONS

Westermarck, et al., "Faecal hydrolase activity as determined by radial enzyme diffusion: a new method for detecting pancreatic dysfunction in the dog", *Res. Vet. Sci.*, vol. 28, No. 3, pp. 341-346, (1980) (Abstract).

Williams, et al., "Comparison of methods for assay of the fecal proteolytic activity", *Vet. Clin. Pathol.*, vol. 19, No. 1, pp. 20-24, (1990) (Abstract).

Williams, et al., "Fecal proteolytic activity in clinically normal cats and in a cat with exocrine pancreatic insufficiency", *J. Am. Vet. Med. Assoc.*, vol. 197, No. 2, pp. 1112-1113, 1116, (1990) (Abstract).

Abdel-Rahman et al., Evaluation of a diagnostic monoclonal antibody-based capture enzyme-linked immunosorbent assay for detection of a 26- to 28-kd *Fasciola hepatica* coproantigen in cattle, *American Journal of Veterinary Research* 59:533-537 (1998).

Bowie et al., *Science*, 1990, vol. 257, pp. 1306-1310.

Bungiro and Cappello, "Detection of Excretory/Secretory Coproantigens in Hookworm infection," *Am. J. Trop. Med. Hyg.* 73(5):915-920 (2005).

Bungiro, Jr., et al., "Purification and Molecular Cloning of and Immunization with *Ancylostoma ceylancium* Excretory-Secretory Protein 2, an Immunocreactive Immunoreactive Protein Produced by Adult Hookworms," *Infection and Immunity* 72(4):2203-2213 (2004).

Carleton et al., Prevalence of *Dirofilaria immitis* and gastrointestinal helminths in cats euthanized at animal control agencies in northwest Georgia, *Veterinary Parisitology* 119:319-326 (2004).

Coulaud, J.P., et al., Albendazole: a new single dose anthelmintic. Study in 1455 patients, *Acta Tropica* 41:87-90 (1984).

De Oliveira et al., IgM-ELISA for diagnosis of schistosomiasis mansoni in low endemic areas, Cadernos de saude publica / Ministério da Saude, Fundacao Oswaldo Cruz, Escola Nacional de Saude Publica 19:255-261 (2003).

Deplazes et al., Detection of *Taenia hydatigena* copro-antigens by ELISA in dogs, *Veterinary Parisitology* 36:91-103 (1990).

Dumenigo et al., Kinetics of antibody-based antigen detection in serum and faeces of sheep experimentally infected with *Fasciola hepatica*, *Veterinary Parisitology* 86:23-31 (1999).

Foreyt, W.J., Veterinary Parasitology Reference Manual, Fifth Edition, 2001, ISBN 0-8138-2419-2, pp. 3-10.

Hill et al., "A *Trichuris* specific diagnostic antigen from culture fluids of *Trichuris suis* adult worms", *Veterinary Parasitology*, vol. 68, pp. 91-102, (1997).

IDEXX Laboratories Canine Paravovirus Antigen Test Kit package insert (English Section Only).

Martinez-Maya et al., Taeniosis and detection of antibodies against Cysticeri among inhabitants of a rural community in Guerro State, Mexico, Salud Publica de Mexico 45:84-89 (2003).

NCBI Blast: SEQ ID No. 4 (Performed Aug. 29, 2009 using http://blast.ncbi.nlm.nih.gov/blast.cgi).

Ott et al., Demonstration of both immunologically unique and common antigenic determinants in *Dirofilaria immitis* and *Toxocara canis* using monoclonal antibodies, *Veterinary Immunology and Immunopathology* 10:147-153 (1985).

Roberts, L.S., et al., Foundations of Parasitology, Fifth Edition, 1996, Library of Congress Card Catalog No. 94-72939, ISBN 0-687-26071-S, pp. 1-4.

Southworth, Exine development in *Gerbera jamesonii* (Asteraceae: Mutisieae), *American Journal of Botany*, 70:1038-1047 (1983).

Voller, "The Enzyme Linked Immunosorbent Assay", *Diagnostic Horizon*, vol. 2, No. 1, pp. 1-7, Feb. 1978.

Willard et al., Diagnosis of Aelurostrongylus abstrusus and *Dirofilaria immitis* infections in cats from a human shelter, *Journal of the American Veterinary Medical Association* 192:913-916 (1988).

Yamasaki et al., "Development of Highly Specific Recombinant *Toxocara canis* Second-Stage Larva Excretory-Secretory Antigen for Immunodiagnosis of Human Toxocariasis," Journal of Clinical Microbiology 38 (4):1409-1413 (2000).

Zhan et at, "Molecular characterisation of the Ancylostoma-secreted protein family from the adult stage of *Ancylostoma caninum*," *International Journal for Parisitology* 33:897-907 (2003).

Bailey, "The Raising of a Polyclonal Antiserum to a Protein", *Methods Mol. Biol.*, vol. 32, pp. 381-388, (1994).

Barker, et al., "Isolation of a gene family that encodes the porin-like proteins from the human parasitic nematode *Trichuris trichiura*", *Gene*, vol. 229, pp. 131-136, (1999).

Dean, "Preparation and Characterization of Monoclonal Antibodies to Proteins and Other Cellular.Components", *Methods Mol. Biol.*, vol. 32, pp. 361-379, (1994).

Dean, "Preparation and Testing of Monoclonal Antibodies to Recombinant Proteins", *Methods Mol. Biol.*, vol. 80, pp. 23-37, (1998).

Drenckhahn, et al., "Production of Polyclonal Antibodies against Proteins and Peptides", *Methods Cell Biol.*, vol. 37, pp. 7-56, (1993).

Dryden, et al., "Comparison of Common Fecal Flotation Techniques for the Recovery of Parasite Eggs and Oocysts", *Vet. Ther.*, vol. 6, No. 1, pp. 15-28, (2005).

Gullick, "Production of Antisera to Synthetic Peptides", *Methods Mol. Biol.*, vol. 32, pp. 389-399, (1994).

Kennedy, "The Nematode Polyprotein Allergens/Antigens", *Parasitol. Today*, vol. 16, No. 9, pp. 373-380, (2000).

Memoranda, "Parasite Antigens", *Bull. World Health Organ*, vol. 52, pp. 237-249, (1975).

Morrison, "In Vitro Antibodies: Strategies for Production and Application", *Annu. Rev. Immunol.*, vol. 10, pp. 239-265, (1992).

Prociv et al., "Human enteric infection with *Ancyostoma caninum*: hookworms reappraised in the light of a "new" zoonosis", *Acta. Tropica.*, vol. 62, pp. 23-44, (1996).

Wright, et al., "Genetically Engineered Antibodies: Progress and Prospects", *Crit. Rev. Immunol.*, vol. 12 (3-4), pp. 125-168, (1992).

Xia, et al., "The ABA-1 allergen of *Ascaris lumbricoides*: sequence polymorphism stage and tissue-specific expression, lipid binding function and protein biophysical properties", *Parasitology*, vol. 120 (Pt.2), pp. 211-224, (2000).

Yahiro, et al., "Identification, characterization and expression of *Toxocara canis* nematode polyprotein allergen TBA-1", *Parasite Immunol.*, vol. 20, No. 8, pp. 351-357, (1998).

Allan, et al., "Coproantigen detection for immunodiagnosis of echinococcosis and taeniasis in dogs and humans", *Parasitology*, 1992, 104:347-355.

Barker, et al., "Isolation of a gene family that encodes the porin-like proteins from the human parasitic nematode *Trichuris trichiura*", Gene, 1999, 229:131-136.

Bethony, et al., "Antibodies against a secreted protein from hookworm larvae reduce the intensity of hookworm infection in humans and vaccinated laboratory animals", *FASEB Journal*, 2005, 19:1743-1745.

Bungiro, et al., "Detection of excretory/secretory coporantigens in experimental hookworm infection", *Am. J. Trop. Med. Hyg.*, 2005, 73(5):915-920.

Bungiro, et al., "Purification and molecular cloning of and immunization with *Ancylostoma ceylanicum* excretory-secretory protein 2, an immunoreactive protein produced by adult hookworms", *Infection and Immunity*, 2004, 72(4):2203-2213.

Croese, et al., "Occult enteric infection by *Ancylostoma caninum*: A previously unrecognized zoonosis", *Gastroenterology*, 1994, 106:3-12.

Daub, et al., "A survey of genes expressed in adults of the human hookworm, Nacator americanus", *Parasitology*, 2000, 120:171-184.

De Oliveira Vasconcelos, et al., "Identification of stage-specific proteins of *Angiostrongylus vasorum* (Baillet, 1866) Kamensky", *Parasitol. Res.*, 2007, 102(3):389-395.

Drake, et al., "Molecular and functional characterization of a recombinant protein of *Trichuris trichiura*", *Proc. Bio. Sci.*, 1998, 265:1559-1565.

Drake, et al., "The major secreted product of the whipworm, *Trichuris*, is a pore-forming protein", *Proc. Bio. Sci*, 1994, 257:255-261.

Gasser, et al., "Improved molecular diagnostic tools for human hookworms", *Expert Rev. Mol. Diagn.*, 2009, 9(1):17-21.

(56) References Cited

OTHER PUBLICATIONS

Jenkins et al., "Functional antigens of *Trichuris muris* released during in vitro maintenance: their immunogenicity and partial purification", *Parasitology*, 1983, 86:73-82.
Johnson, et al., "Detection of gastrointestinal nematodes by a coproantigen capture ELISA", *Res. Vet. Sci.*, 1996, 60:7-12.
Kania et al., "Anoplocephala perfoliata coproantigen detection: a preliminary study", *Vet. Parasitol.*, 2005, 127(2): 115-119.
Lillywhite et al., "Humoral immune responses in human infection with the whipworm *Trichuris trichiura*", *Parasite Immunol*., 1991, 13:491-507.
Lillywhite et al., "Identification and characterization of excreted/secreted products of *Trichuris trichiura*", *Parasite Immunol.*, 1995, 17:47-54.
Nukumi et al., "Whey acidic protein (WAP) regulates the proliferation of mammary epithelial cells by preventing serine protease from degrading laminin", *J. Cell. Physiol.*, May 31, 2007, 213:793-800.
Parkinson et al., "400 000 nematode ESTs on the Net", *Trends Parasitol.*, Jul. 2003, 19(7):283-286.
Song et al., "Cross-reactivity between sera from dogs experimentally infected with *Dirofilaria immitis* and crude extract of *Toxocara canis*", *Korean J. Parasitol.*, Dec. 2002, 40(4):195-198.
Traub, et al., "Canine gastrointestinal parasitic zoonoses in India", *Trends in Parasit.*, 2005, 21(1):42-48.
Wakelin, "Acquired immunity to *Trichuris muris* in the albino laboratory mouse", *Parasitology*, 1967, 57:515-524.
GenBank Accession No. AAD01628.1. Jan. 1999. [Retrieved from the Internet Feb. 25, 2010: <URL:http://ncbi.nlm.nih.gov/protein/410955>].
GenBank Accession No. BM965689.1. Mar. 2002. [Retrieved from the Internet Feb. 25, 2010: <URL:http://ncbi.nlm.nih.gov/nucest/19558140>].
GenBank Accession No. BQ088667.1. Apr. 2002. [Retrieved from the Internet Feb. 25, 2010: <URL:http://ncbi.nlm.nih.gov/nucest/20062868>].
GenBank Accession No. AAC17174.1. May 1998. [Retrieved from the Internet Feb. 25, 2010: <URL:http://ncbi.nlm.nih.gov/protein/3152922>].
GenBank Accession No. AAC47345.1. Oct. 2007. [Retrieved from the Internet Feb. 25, 2010: <URL:http://ncbi.nlm.nih.gov/protein/1663728>].
GenBank Accession No. AAG31482.1. Nov. 2000. [Retrieved from the Internet Feb. 25, 2010: <URL:http://ncbi.nlm.nih.gov/protein/11138792>].
GenBank Accession No. NP_510821. Nov. 2008. [Retrieved from the Internet Feb. 25, 2010: <URL:http://ncbi.nlm.nih.gov/protein/17551598>].
GenBank Accession No. CB098869. Jan. 28, 2003. [Retrieved from the Internet Mar. 30, 2010: <URL:http://ncbi.nlm.nih.gov/nucest/27924676>].
GenBank Accession No. CB099165. Jan. 28, 2003. [Retrieved from the Internet Mar. 30, 2010: <URL:http://ncbi.nlm.nih.gov/nucest/27924972>].
GenBank Accession No. CB099244. Jan. 28, 2003. [Retrieved from the Internet Mar. 30, 2010: <URL:http://ncbi.nlm.nih.gov/nucest/27925051>].
GenBank Accession No. CB099367. Jan. 28, 2003. [Retrieved from the Internet Mar. 30, 2010: <URL:http://ncbi.nlm.nih.gov/nucest/27925174>].
GenBank Accession No. CB188155. Feb. 5, 2003. [Retrieved from the Internet Mar. 30, 2010: <URL:http://ncbi.nlm.nih.gov/nucest/28251547>].
GenBank Accession No. CB188174. Feb. 5, 2003. [Retrieved from the Internet Mar. 30, 2010: <URL:http://ncbi.nlm.nih.gov/nucest/28251566>].
GenBank Accession No. CB188239. Feb. 5, 2003. [Retrieved from the Internet Mar. 30, 2010: <URK:http://ncbi.nlm.nih.gov/nucest/28251631>].
GenBank Accession No. CB188637. Feb. 5, 2003. [Retrieved from the Internet Mar. 30, 2010: <URL:http://ncbi.nlm.nih.gov/nucest/28252029>].
GenBank Accession No. CB189034. Feb. 5, 2003. [Retrieved from the Internet Mar. 30, 2010: <URL:http://ncbi.nlm.nih.gov/nucest/28252426>].
GenBank Accession No. CB189036. Feb. 5, 2003. [Retrieved from the Internet Mar. 30, 2010: <URL:http://ncbi.nlm.nih.gov/nucest/28252428>].
GenBank Accession No. CB189116. Feb. 5, 2003. [Retrieved from the Internet Mar. 30, 2010: <URL:http://ncbi.nlm.nih.gov/nucest/28252508>].
GenBank Accession No. CB189285. Feb. 5, 2003. [Retrieved from the Internet Mar. 30, 2010: <URL:http://ncbi.nlm.nih.gov/nucest/28252677>].
GenBank Accession No. CB189434. Feb. 5, 2003. [Retrieved from the Internet Mar. 30, 2010: <URL:http://ncbi.nlm.nih.gov/nucest/28252826>].
GenBank Accession No. CB277501. Feb. 25, 2003. [Retrieved from the Internet Mar. 30, 2010: <URL:http://ncbi.nlm.nih.gov/nucest/28561086>].
GenBank Accession No. CB277590. Feb. 25, 2003. [Retrieved from the Internet Mar. 30, 2010: <URL:http://ncbi.nlm.nih.gov/nucest/28561175>].
GenBank Accession No. CB277641. Feb. 25, 2003. [Retrieved from the Internet Mar. 30, 2010: <URL:http://ncbi.nlm.nih.gov/nucest/28561226>].
GenBank Accession No. CB277653. Feb. 25, 2003. [Retrieved from the Internet Mar. 30, 2010: <URL:http://ncbi.nlm.nih.gov/nucest/28561238>].
GenBank Accession No. CB277950. Feb. 25, 2003. [Retrieved from the Internet Mar. 30, 2010: <URL:http://ncbi.nlm.nih.gov/nucest/28561535>].
GenBank Accession No. CB188241. Feb. 5, 2003. [Retrieved from the Internet Mar. 30, 2010: <URL:http://ncbi.nlm.nih.gov/nucest/28251633>].
GenBank Accession No. CB277846. Feb. 25, 2003. [Retrieved from the Internet Mar. 30, 2010: <URL:http://ncbi.nlm.nih.gov/nucest/28561431>].
GenBank Accession No. CB277826. Feb. 25, 2003. [Retrieved from the Internet Mar. 30, 2010: <URL:http://ncbi.nlm.nih.gov/nucest/28561411>].
GenBank Accession No. CB189366. Feb. 5, 2003. [Retrieved from the Internet Mar. 30, 2010: <URL:http://ncbi.nlm.nih.gov/nucest/28252758>].
GenBank Accession No. CB098807. Jan. 28, 2003. [Retrieved from the Internet Mar. 30, 2010: <URL:http://ncbi.nlm.nih.gov/nucest/27924614>].
GenBank Accession No. CB189370. Feb. 5, 2003. [Retrieved from the Internet Mar. 30, 2010: <URL:http://ncbi.nlm.nih.gov/nucest/28252762>].
GenBank Accession No. BQ089025. Apr. 5, 2002. [Retrieved from the Internet Mar. 30, 2010: <URL:http://ncbi.nlm.nih.gov/nucest/20063226>].
GenBank Accession No. BM966041. Mar. 20, 2002. [Retrieved from the Internet Mar. 30, 2010: <URL:http://ncbi.nlm.nih.gov/nucest/19558790>].
GenBank Accession No. BQ088880. Apr. 5, 2002. [Retrieved from the Internet Mar. 30, 2010: <URL:http://ncbi.nlm.nih.gov/nucest/20063081>].
Uniprot submission P07852. Aug. 1988. [Retrieved from the Internet Mar. 30, 2010: <URL: http://www.uniprot.org/uniprot/P07852>].
Uniprot submission Q06811. Nov. 1997. [Retrieved from the Internet Feb. 25, 2010: <URL://www.uniprot.org/uniprot/Q06811>].
Uniprot submission Q24702. Nov. 1996. [Retrieved from the Internet Feb. 25, 2010: <URL:http://uniprot.org/uniprot/Q24702>].
Uniprot submission P91811. May 1997. [Retrieved from the Internet Feb. 25, 2010: <URL:http://uniprot.org/uniprot/P91811>].
Uniprot submission O44397. Jun. 1988. [Retrieved from the Internet Nov. 11, 2009: <URL:http://uniprot.org/uniprot/044397>].
Uniprot submission P19398. Nov. 1, 1990. [Retrieved from the Internet Mar. 30, 2010: <URL: http://www.uniprot.org/uniprot/P19398>].

(56) References Cited

OTHER PUBLICATIONS

Uniprot submission O77416. Nov. 1, 1998. [Retrieved from the Internet Mar. 30, 2010: <URL: http://www.uniprot.org/uniprot/O77416>].

Uniprot submission Q2VMT7. Jan. 10, 2006. [Retrieved from the Internet Mar. 30, 2010: <URL: http://www.uniprot.org/uniprot/Q2VMT7>].

Uniprot submission Q9U6V1. May 1, 2000. [Retrieved from the Internet Mar. 30, 2010: <URL: http://www.uniprot.org/uniprot/Q9U6V1>].

Uniprot submission Q16938. Nov. 1, 1996. [Retrieved from the Internet Mar. 30, 2010: <URL: http://www.uniprot.org/uniprot/Q16938>].

Uniprot submission Q962V8. Dec. 1, 2001. [Retrieved from the Internet Mar. 30, 2010: <URL: http://www.uniprot.org/uniprot/Q962V8>].

```
agtcagtagc cactttaatc catcagaatg ctctctgttc ttgcgctttt cgctcttatt    60
acttttgctg tggccggtcc ggaaagctgc ggtccaaacg aagtgtggac tgaatgtacc   120
ggttgcgaat tgaaatgtgg gcaagatgaa aatacgccgt gcacactaaa ctgtcgaccg   180
ccgtcatgtg agtgctctcc aggaagaggc atgagacgaa ccaacgatgg aaggtgcatt   240
ccggctagtc agtgcccgca acacagggcc aagagagagg agcaatgcaa gccaaatgag   300
cagtggtcac cgtgccgagg atgtgaagga acatgcgcac aaagatttgt cccttgcact   360
agaaactgcc gaccaccagg ctgtgaatgc gttgctggcg caggtttcgt acgtgacgct   420
gaaggaaact gcatcaagtt cgacgattgc ccgaagtaaa taataaccat acaaattgct   480
gattccaatt aaaataataa atgagtccag ctgttaaaaa aaaaaaaaaa aaaaa        535
```

(SEQ ID NO:1)

FIG. 1

```
cagtcagcag ctacttttat ccatcggaat gctctctgtt cttgcgcttt tcgctcttat      60
tactttcgct gtggccgatc cgaaaagttg cggtccaaac gaagtgtgga ctgaatgtac     120
cggttgcgag ttgaaatgcg ggcaggatga ggatacgccg tgcacactaa actgtcggcc     180
gccgtcatgt gagtgctcac caggaagagg catgagacga accgacgatg ggaggtgcat     240
tccggctagt cagtgcccgc aacacagagc caagagagag gagcagtgca agccaaatga     300
gcagtggtca ccgtgccgag gatgtgaagg aacatgcgca caaagatttg tcccttgcac     360
tagaaactgc cgaccaccag gatgtgaatg cgttgctggc gcaggtttcg tacgtgacgc     420
tgcaggaaat tgcatcaagt tcgacgattg cccgaagtaa ataataacca tactaattgc     480
tgattacaat taaaataata aatgagtcca gctgttaaaa aaaaaaaaaa aaaaaa         536
```

(SEQ ID NO:2)

FIG. 2

```
agtcagtagc cactttaatc catcagaatg ctctctgttc ttgcgctttt cgctcttatt      60
                              M   L   S   V   L   A   L   F   A   L   I   11
acttttgctg tggccggtcc ggaaagctgc ggtccaaacg aagtgtggac tgaatgtacc     120
 T   F   A   V   A   G   P   E   S   C   G   P   N   E   V   W   T   E   C   T    31
ggttgcgaat tgaaatgtgg gcaagatgaa aatacgccgt gcacactaaa ctgtcgaccg     180
 G   C   E   L   K   C   G   Q   D   E   N   T   P   C   T   L   N   C   R   P    51
ccgtcatgtg agtgctctcc aggaagaggc atgagacgaa ccaacgatgg aaggtgcatt     240
 P   S   C   E   C   S   P   G   R   G   M   R   R   T   N   D   G   R   C   I    71
ccggctagtc agtgcccgca acacagggcc aagagagagg agcaatgcaa gccaaatgag     300
 P   A   S   Q   C   P   Q   H   R   A   K   R   E   E   Q   C   K   P   N   E    91
cagtggtcac cgtgccgagg atgtgaagga acatgcgcac aaagatttgt cccttgcact     360
 Q   W   S   P   C   R   G   C   E   G   T   C   A   Q   R   F   V   P   C   T   111
agaaactgcc gaccaccagg ctgtgaatgc gttgctggcg caggtttcgt acgtgacgct     420
 R   N   C   R   P   P   G   C   E   C   V   A   G   A   G   F   V   R   D   A   131
gaaggaaact gcatcaagtt cgacgattgc ccgaagtaaa taataaccat acaaattgct     480
 E   G   N   C   I   K   F   D   D   C   P   K   *                               143
gattccaatt aaaataataa atgagtccag ctgttaaaaa aaaaaaaaaa aaaaa          535

(Nucleotide sequence is SEQ ID NO:1; Amino acid sequence is SEQ ID NO:3)
```

FIG. 3

```
cagtcagcag ctacttttat ccatcggaat gctctctgtt cttgcgcttt tcgctcttat      60
                              M   L   S   V   L   A   L   F   A   L   I    11
tactttcgct gtggccgatc cgaaaagttg cggtccaaac gaagtgtgga ctgaatgtac     120
 T   F   A   V   A   D   P   K   S   C   G   P   N   E   V   W   T   E   C   T    31
cggttgcgag ttgaaatgcg ggcaggatga ggatacgccg tgcacactaa actgtcggcc     180
 G   C   E   L   K   C   G   Q   D   E   D   T   P   C   T   L   N   C   R   P    51
gccgtcatgt gagtgctcac caggaagagg catgagacga accgacgatg ggaggtgcat     240
 P   S   C   E   C   S   P   G   R   G   M   R   R   T   D   D   G   R   C   I    71
tccggctagt cagtgcccgc aacacagagc caagagagag gagcagtgca agccaaatga     300
 P   A   S   Q   C   P   Q   H   R   A   K   R   E   Q   C   K   P   N   E    91
gcagtggtca ccgtgccgag gatgtgaagg aacatgcgca caaagatttg tcccttgcac     360
 Q   W   S   P   C   R   G   C   E   G   T   C   A   Q   R   F   V   P   C   T   111
tagaaactgc cgaccaccag gatgtgaatg cgttgctggc gcaggtttcg tacgtgacgc     420
 R   N   C   R   P   P   G   C   E   C   V   A   G   A   G   F   V   R   D   A   131
tgcaggaaat tgcatcaagt tcgacgattg cccgaagtaa ataataacca tactaattgc     480
 A   G   N   C   I   K   F   D   D   C   P   K   *                                143
tgattacaat taaaataata aatgagtcca gctgttaaaa aaaaaaaaa aaaaaa           536
```

(Nucleotide sequence is SEQ ID NO:2; Amino acid sequence is SEQ ID NO:4)

FIG. 4

MGPESCGPNEVWTECTGCELKCGQDENTPCTLNCRPPSCECSPGRGMRRTNDGRCIPASQCP
QHRAKREEQCKPNEQWSPCRGCEGTCAQRFVPCTRNCRPPGCECVAGAGFVRDAEGNCIK
FDDCPK (SEQ ID NO: 5)

FIG. 19

```
6728N   MGP---ESCGPNEVWTECTGCELKCGQDENTPCTLNCRPPSCECSPGRGMRRTNDGRCIPASQCPQH 64  (SEQ ID NO: 10)
6728C   MRAKREEQCKPNEQWSPCRGCEGTCAQR-FVPCTRNCRPPGCECVAGAGFVRDAEGNCIKFDDCPK- 65  (SEQ ID NO: 11)
        *  *.* ***  *:  * ***   .*.:   .  .*** *:****.***.*.*   *:.** :::*:
```

FIG. 20

SEQUENCE LISTING

```
<160> NUMBER OF SEQ ID NOS: 11

<210> SEQ ID NO 1
<211> LENGTH: 535
<212> TYPE: DNA
<213> ORGANISM: Toxocara canis

<400> SEQUENCE: 1
agtcagtagc cactttaatc catcagaatg ctctctgttc ttgcgctttt cgctcttatt      60
acttttgctg tggccggtcc ggaaagctgc ggtccaaacg aagtgtggac tgaatgtacc     120
ggttgcgaat tgaaatgtgg gcaagatgaa aatacgccgt gcacactaaa ctgtcgaccg     180
ccgtgatgtg agtgctctcc aggaagaggc atgagacgaa ccaacgatgg aaggtgcatt     240
ccggctagtc agtgcccgca acacagggcc aagagagagg agcaatgcaa gccaaatgag     300
cagtggtcac cgtgccgagg atgtgaagga acatgcgcac aaagatttgt cccttgcact     360
agaaactgcc gaccaccagg ctgtgaatgc gttgctggcg caggtttcgt acgtgacgct     420
gaaggaaact gcatcaagtt cgacgattgc ccgaagtaaa taataaccat acaaattgct     480
gattccaatt aaaataataa atgagtccag ctgttaaaaa aaaaaaaaa aaaaa          535

<210> SEQ ID NO 2
<211> LENGTH: 536
<212> TYPE: DNA
<213> ORGANISM: Toxocara cati

<400> SEQUENCE: 2
cagtcagcag ctacttttat ccatcggaat gctctctgtt cttgcgcttt tcgctcttat      60
tactttcgct gtggccgatc cgaaaagttg cggtccaaac gaagtgtgga ctgaatgtac     120
cggttgcgag ttgaaatgcg ggcaggatga ggatacgccg tgcacactaa actgtcggcc     180
gccgtcatgt gagtgctcac caggaagagg catgagacga accgacgatg ggaggtgcat     240
tccggctagt cagtgcccgc aacacagagc caagagagag gagcagtgca agccaaatga     300
gcagtggtca ccgtgccgag gatgtgaagg aacatgcgca caaagatttg tcccttgcac     360
tagaaactgc cgaccaccag gatgtgaatg cgttgctggc gcaggtttcg tacgtgacgc     420
tgcaggaaat tgcatcaagt tcgacgattg cccgaagtaa ataataacca tactaattgc     480
tgattacaat taaaataata aatgagtcca gctgttaaaa aaaaaaaaaa aaaaaa       536

<210> SEQ ID NO 3
<211> LENGTH: 143
<212> TYPE: PRT
<213> ORGANISM: Toxocara canis

<400> SEQUENCE: 3
```

Met Leu Ser Val Leu Ala Leu Phe Ala Leu Ile Thr Phe Ala Val Ala
1               5                   10                  15

Gly Pro Glu Ser Cys Gly Pro Asn Glu Val Trp Thr Glu Cys Thr Gly
            20                  25                  30

Cys Glu Leu Lys Cys Gly Gln Asp Glu Asn Thr Pro Cys Thr Leu Asn
        35                  40                  45

Cys Arg Pro Pro Ser Cys Glu Cys Ser Pro Gly Arg Gly Met Arg Arg
    50                  55                  60

Thr Asn Asp Gly Arg Cys Ile Pro Ala Ser Gln Cys Pro Gln His Arg
65                  70                  75                  80

Ala Lys Arg Glu Glu Gln Cys Lys Pro Asn Glu Gln Trp Ser Pro Cys
            85                  90                  95

Arg Gly Cys Glu Gly Thr Cys Ala Gln Arg Phe Val Pro Cys Thr Arg
            100                 105                 110

Asn Cys Arg Pro Pro Gly Cys Glu Cys Val Ala Gly Ala Gly Phe Val
        115                 120                 125

Arg Asp Ala Glu Gly Asn Cys Ile Lys Phe Asp Asp Cys Pro Lys
    130                 135                 140

<210> SEQ ID NO 4
<211> LENGTH: 143
<212> TYPE: PRT
<213> ORGANISM: Toxocara cati

<400> SEQUENCE: 4

Met Leu Ser Val Leu Ala Leu Phe Ala Leu Ile Thr Phe Ala Val Ala
1               5                   10                  15

Asp Pro Lys Ser Cys Gly Pro Asn Glu Val Trp Thr Glu Cys Thr Gly
20 25 30

Cys Glu Leu Lys Cys Gly Gln Asp Glu Asp Thr Pro Cys Thr Leu Asn
35 40 45

Cys Arg Pro Pro Ser Cys Glu Cys Ser Pro Gly Arg Gly Met Arg Arg
50 55 60

Thr Asp Asp Gly Arg Cys Ile Pro Ala Ser Gln Cys Pro Gln His Arg
65 70 75 80

Ala Lys Arg Glu Glu Gln Cys Lys Pro Asn Glu Gln Trp Ser Pro Cys
85 90 95

Arg Gly Cys Glu Gly Thr Cys Ala Gln Arg Phe Val Pro Cys Thr Arg
100 105 110

Asn Cys Arg Pro Pro Gly Cys Glu Cys Val Ala Gly Ala Gly Phe Val
115 120 125

Arg Asp Ala Ala Gly Asn Cys Ile Lys Phe Asp Asp Cys Pro Lys
130 135 140

<210> SEQ ID NO 5
<211> LENGTH: 128
<212> TYPE: PRT
<213> ORGANISM: Artificial
<220> FEATURE:
<223> OTHER INFORMATION: Synthetic

<400> SEQUENCE: 5

Met Gly Pro Glu Ser Cys Gly Pro Asn Glu Val Trp Thr Glu Cys Thr
1 5 10 15

Gly Cys Glu Leu Lys Cys Gly Gln Asp Glu Asn Thr Pro Cys Thr Leu
20 25 30

Asn Cys Arg Pro Pro Ser Cys Glu Cys Ser Pro Gly Arg Gly Met Arg

```
                35                  40                  45
Arg Thr Asn Asp Gly Arg Cys Ile Pro Ala Ser Gln Cys Pro Gln His
            50                  55                  60
Arg Ala Lys Arg Glu Glu Gln Cys Lys Pro Asn Glu Gln Trp Ser Pro
65                  70                  75                  80
Cys Arg Gly Cys Glu Gly Thr Cys Ala Gln Arg Phe Val Pro Cys Thr
                85                  90                  95
Arg Asn Cys Arg Pro Pro Gly Cys Glu Cys Val Ala Gly Ala Gly Phe
            100                 105                 110
Val Arg Asp Ala Glu Gly Asn Cys Ile Lys Phe Asp Asp Cys Pro Lys
        115                 120                 125

<210> SEQ ID NO 6
<211> LENGTH: 127
<212> TYPE: PRT
<213> ORGANISM: Artificial
<220> FEATURE:
<223> OTHER INFORMATION: Synthetic

<400> SEQUENCE: 6

Gly Pro Glu Ser Cys Gly Pro Asn Glu Val Trp Thr Glu Cys Thr Gly
1               5                   10                  15
Cys Glu Leu Lys Cys Gly Gln Asp Glu Asn Thr Pro Cys Thr Leu Asn
            20                  25                  30
Cys Arg Pro Pro Ser Cys Glu Cys Ser Pro Gly Arg Gly Met Arg Arg
        35                  40                  45
Thr Asn Asp Gly Arg Cys Ile Pro Ala Ser Gln Cys Pro Gln His Arg
    50                  55                  60
Ala Lys Arg Glu Glu Gln Cys Lys Pro Asn Glu Gln Trp Ser Pro Cys
65                  70                  75                  80
Arg Gly Cys Glu Gly Thr Cys Ala Gln Arg Phe Val Pro Cys Thr Arg
                85                  90                  95
Asn Cys Arg Pro Pro Gly Cys Glu Cys Val Ala Gly Ala Gly Phe Val
            100                 105                 110
Arg Asp Ala Glu Gly Asn Cys Ile Lys Phe Asp Asp Cys Pro Lys
        115                 120                 125

<210> SEQ ID NO 7
<211> LENGTH: 143
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
```

<400> SEQUENCE: 7

```
Xaa Xaa Xaa Xaa Xaa Xaa Xaa Xaa Xaa Xaa Xaa Xaa Xaa Xaa Xaa
1               5                   10                  15

Xaa Pro Xaa Ser Cys Gly Pro Asn Glu Val Trp Thr Glu Cys Thr Gly
            20                  25                  30

Cys Glu Leu Lys Cys Gly Gln Asp Glu Xaa Thr Pro Cys Thr Leu Asn
            35                  40                  45

Cys Arg Pro Pro Ser Cys Glu Cys Ser Pro Arg Gly Met Arg Arg
50                  55                  60

Thr Xaa Asp Gly Arg Cys Ile Pro Ala Ser Gln Cys Pro Gln His Arg
65                  70                  75                  80

Ala Lys Arg Glu Glu Gln Cys Lys Pro Asn Glu Gln Trp Ser Pro Cys
                85                  90                  95

Arg Gly Cys Glu Gly Thr Cys Ala Gln Arg Phe Val Pro Cys Thr Arg
                100                 105                 110

Asn Cys Arg Pro Pro Gly Cys Glu Cys Val Ala Gly Ala Gly Phe Val
            115                 120                 125

Arg Asp Ala Xaa Gly Asn Cys Ile Lys Phe Asp Cys Pro Lys
            130                 135                 140
```

<210> SEQ ID NO 8
<211> LENGTH: 8
<212> TYPE: PRT
<213> ORGANISM: Artificial
<220> FEATURE:
<223> OTHER INFORMATION: Synthetic

<400> SEQUENCE: 8

```
Arg Phe Val Pro Cys Thr Arg Asn
1               5
```

<210> SEQ ID NO 9
<211> LENGTH: 10
<212> TYPE: PRT
<213> ORGANISM: Artificial
<220> FEATURE:
<223> OTHER INFORMATION: Synthetic

<400> SEQUENCE: 9

```
Arg Asp Ala Glu Gly Asn Cys Ile Lys Phe
1               5                   10
```

<210> SEQ ID NO 10
<211> LENGTH: 64
<212> TYPE: PRT
<213> ORGANISM: Artificial
<220> FEATURE:
<223> OTHER INFORMATION: Synthetic

<400> SEQUENCE: 10

```
Met Gly Pro Glu Ser Cys Gly Pro Asn Glu Val Trp Thr Glu Cys Thr
1               5                   10                  15

Gly Cys Glu Leu Lys Cys Gly Gln Asp Glu Asn Thr Pro Cys Thr Leu
                20                  25                  30

Asn Cys Arg Pro Pro Ser Cys Glu Cys Ser Pro Gly Gly Met Arg
            35                  40                  45

Arg Thr Asn Asp Gly Arg Cys Ile Pro Ala Ser Gln Cys Pro Gln His
50                  55                  60
```

<210> SEQ ID NO 11

```
<211> LENGTH: 65
<212> TYPE: PRT
<213> ORGANISM: Artificial
<220> FEATURE:
<223> OTHER INFORMATION: Synthetic

<400> SEQUENCE: 11

Met Arg Ala Lys Arg Glu Glu Gln Cys Lys Pro Asn Glu Gln Trp Ser
1               5                   10                  15

Pro Cys Arg Gly Cys Glu Gly Thr Cys Ala Gln Arg Phe Val Pro Cys
            20                  25                  30

Thr Arg Asn Cys Arg Pro Pro Gly Cys Glu Cys Val Ala Gly Ala Gly
            35                  40                  45

Phe Val Arg Asp Ala Glu Gly Asn Cys Ile Lys Phe Asp Asp Cys Pro
    50                  55                  60

Lys
65
```

METHODS, DEVICES, KITS AND COMPOSITIONS FOR DETECTING ROUNDWORM

CROSS REFERENCE

This application is a divisional of U.S. patent application Ser. No. 12/467,808, filed May 18, 2009, now U.S. Pat. No. 8,580,518, which claims the benefit of priority to U.S. Provisional Patent Application Ser. No. 61/128,099, filed May 19, 2008, which is incorporated by reference herein in its entirety.

BACKGROUND OF THE INVENTION

1. Field of the Invention

The present invention relates to compositions, devices, kits and methods for the detection of roundworm in mammals. More particularly, the present invention relates to polypeptides and polypeptide compositions, antibodies and antibody compositions, devices, kits, and methods for detecting the presence or absence of roundworm antigen in a sample from a mammal that may also include one or more of hookworm, whipworm, and heartworm antigen.

2. Description of the Prior Art

Adult roundworms live in the small intestine and lay eggs that pass out in the feces. In the environment, infective larvae remain within the eggs and develop into an infective stage after approximately three weeks at optimal temperatures. The infective eggs enter a host by ingestion and hatch in the small intestine. In dogs less than five weeks of age, larvae migrate through the tissue and into the bloodstream before eventually reaching the lung and trachea where additional development occurs. The host coughs up and swallows the larvae, which molt into adults that reside in small intestine. Larvae that hatch within dogs greater than five weeks of age or within other animals, including humans, are capable of traveling to a wide range of tissues including the liver, lungs, heart, brain, and skeletal muscle. These larvae subsequently arrest their development and encyst in the tissue of the host. In pregnant and lactating dogs, encysted larvae can become reactivated and cause intestinal infection in the mother, migrate to the uterus and directly infect the fetus through the placenta, or migrate to the mammary tissue and infect nursing animals. Parasitic roundworms cause disease not only in their animal hosts, but are also the etiological agents of larval migrans syndrome as well as severe enteritis and allergic reactions in humans, which occurs after ingestion of infectious eggs from the environment or ingestion of larvae found within liver, meat or other tissues of paratenic hosts.

Intestinal roundworm infection is common in animals and, if left untreated, can cause serious disease and even death. Although it is relatively easy to diagnose a roundworm-infected animal as having a parasitic worm (helminth) infection of some type, it is significantly more difficult to identify roundworm, specifically, as the causative worm. This is a problem because roundworm infections are best treated when the infected animal's caregiver has knowledge that roundworm is the specific source of the infection. In addition, humans who may come in contact with the infested animal or its excretions may be advised to take precautions against acquiring the parasite. In this context, it is important to determine the worm species with high specificity, as some helminths, such as roundworms and hookworms, can cause significant disease (e.g., larva migrans) in humans, while it is generally accepted that whipworm does not play a zoonotic role of importance in humans.

Current methods for diagnosis of roundworm infections primarily involve microscopic examination of fecal samples, either directly in fecal smears or following concentration of ova by flotation in density media. Despite this procedure's high adoption, the method has significant shortcomings. These microscopic methods are time consuming, are unpleasant, require specialized equipment and can have low specificity [Dryden et al., 2005, Vet Therap. 6(1), 15-28]. In addition, the accuracy of results of these methods is highly dependent upon the skill and expertise of the operator.

Stool handling is disagreeable and hazardous. Sanitary and inoffensive procedures for processing stool are awkward and often complex. Such procedures may include weighing, centrifuging and storing, and are difficult except in a clinical laboratory equipped with a suitable apparatus, protective equipment, and a skilled technician. Therefore, any reduction in the number of steps required to perform a fecal test and any reduction in contact between test operator and the test material is desirable. Clinical laboratories have been using the immunoassay methods for the detection of various viruses, bacteria and non-helminth parasites and organisms in feces. However, there remains a need for a simple immunoassay method for the detection of a parasitic worm infection, and roundworm infection in particular in feces, whole blood or in serum.

SUMMARY OF THE INVENTION

In one aspect, the invention includes antibodies that specifically bind to a polypeptide including all or an antigenic portion of the amino acid sequence that corresponds to SEQ ID NO:3, SEQ ID NO:4, SEQ ID NO:5, SEQ ID NO:6, SEQ ID NO:7, as listed herein, or to a polypeptide including a sequence that is a conservative variant of one of those sequences. In a further aspect, the antibodies specifically bind to antigen from roundworm infested mammals, but do not specifically bind antigen from mammals infected with hookworm, heartworm and/or whipworm.

In another aspect, the invention includes antibodies that are obtained by immunization with the polypeptide including all or an antigenic portion of the amino acid sequence that corresponds to SEQ ID NO:3, SEQ ID NO:4, SEQ ID NO:5, SEQ ID NO:6 or SEQ ID NO:7, or with a polypeptide including a sequence that is a conservative variant of one of those sequences.

In yet another aspect, the invention provides a device for detecting the presence or absence of roundworm antigens from a sample; the device comprising a solid support, wherein the solid support has immobilized thereon one or more antibodies that are capable of specifically binding to a polypeptide that has an amino acid sequence that corresponds to SEQ ID NO:3, SEQ ID NO:4, SEQ ID NO:5, SEQ ID NO:6, SEQ ID NO:7, or an antigenic portion thereof. The device, may be, but is not limited to being, for example, an ELISA device, such as a lateral flow immunoassay device or microtiter plate device. Mammalian samples that may be tested for roundworm by the device include, but are not limited to being, feces, whole blood, serum, mammary milk and whole tissue, such as tissue from mammary gland, intestine, liver, heart, lung, esophagus, brain, muscle, and eye, for example. The device further may include, but need not include, one or more reagents for the detection of one or more of the group consisting of: one or more non-roundworm worm parasites, one or more non-worm parasites, one or more viruses, one or more fungi, and one or more bacteria.

In yet another aspect, the invention provides a method of detecting the presence or absence of roundworm, such as Toxocara canis (*T. canis*), Toxocara cati (*T. cati*), Toxocara vitulorum (*T. vitulorum*), Toxascaris leonina (*T. leonina*) Baylisascaris procyonis (*B. procyonis*), Ascaridia galli (*A. galli*), Parascaris equorum (*P. equorum*), Ascaris suum (*A. suum*), Ascaris lumbicoides (*A. lumbricoides*), Anisakis simplex (*A. simplex*), or Pseudoterranova decipiens (*P. decipiens*), for example, in a sample. The sample can be obtained from a mammal, such as a canine, feline, porcine, bovine, human, cetacean, or pinniped. In one aspect, the method is carried out to test a fecal sample for roundworm coproantigen. The method, however, is not limited to being carried out to test a fecal sample. In addition to feces, the sample therefore may be, but is not limited to being whole blood, serum, mammary milk and whole tissue, such as tissue from mammary gland, intestine, liver, heart, lung, esophagus, brain, muscle, and eye, for example. Steps of the method include contacting the sample with one or more of the antibodies of the invention; forming antibody polypeptide complexes in the presence of the polypeptides if any, in the sample; and detecting the presence or absence of the antibody-polypeptide complexes, if any. The method further may include one or more of the optional steps of diagnosing the mammal as either having or not having a roundworm infection and determining whether a nucleic acid from roundworm is present in the same sample that was contacted with the antibodies for the purpose of detecting the presence or absence of roundworm or in some other sample from the mammal. The method may also be used to test for environmental contamination with roundworm. Environmental samples that may be tested for roundworm by the device include, but are not limited to soil, decomposing material, or fecal matter from residential settings including yards, gardens, sand boxes, and playgrounds. Testing locations may also include parks, beaches, forests, farms, or other locations exposed to fecal material from dogs, cats, or other mammalian hosts of roundworms. Feces from indoor and outdoor litter boxes may also be tested.

In yet another aspect, the present invention includes a kit for carrying out one or more steps of the method of the invention. The kit may optionally include, for example, the device and one or more of the compositions of the present invention and instructions for carrying out the method of the present invention. The kit may further optionally include, for example, one or more indicator reagents, one or more antibody labeling compounds, one or more antibodies, one or more antigen capture reagents, one or more inhibitors, and one or more wash reagents to be used as part of the device and/or to be used in carrying out the method.

BRIEF DESCRIPTION OF THE DRAWINGS

FIG. 1 shows the nucleotide sequence of a 535-nucleotide cDNA sequence from whole adult *Toxocara canis*. (SEQ ID NO:1).

FIG. 2 shows the nucleotide sequence of a 536-nucleotide cDNA sequence from whole adult *Toxocara cati*. (SEQ ID NO:2).

FIG. 3 shows the amino acid sequence (SEQ ID NO:3) of a large ORF of SEQ ID NO:1. The stop codon is indicated by *.

FIG. 4 shows the amino acid sequence (SEQ ID NO:4) of a large ORF of SEQ ID NO:2. The stop codon is indicated by *.

FIG. 19. shows the amino acid sequence of the full length DIV6728 (SEQ ID NO: 5) with the two peptides (SEQ ID NO: 8 and SEQ ID NO: 9) identified by Mass Spectrometry analysis identified by highlighting them in the shaded boxes following the method of the present invention in the seventh Example.

FIG. 20 shows an alignment of the 6728N (SEQ ID NO: 10) and 6728C (SEQ ID NO: 11) amino acid sequences encoded by the constructs following the method of the present invention in the eighth Example.

DETAILED DESCRIPTION OF THE PREFERRED EMBODIMENTS OF THE INVENTION

I. Introduction

Figure 5:
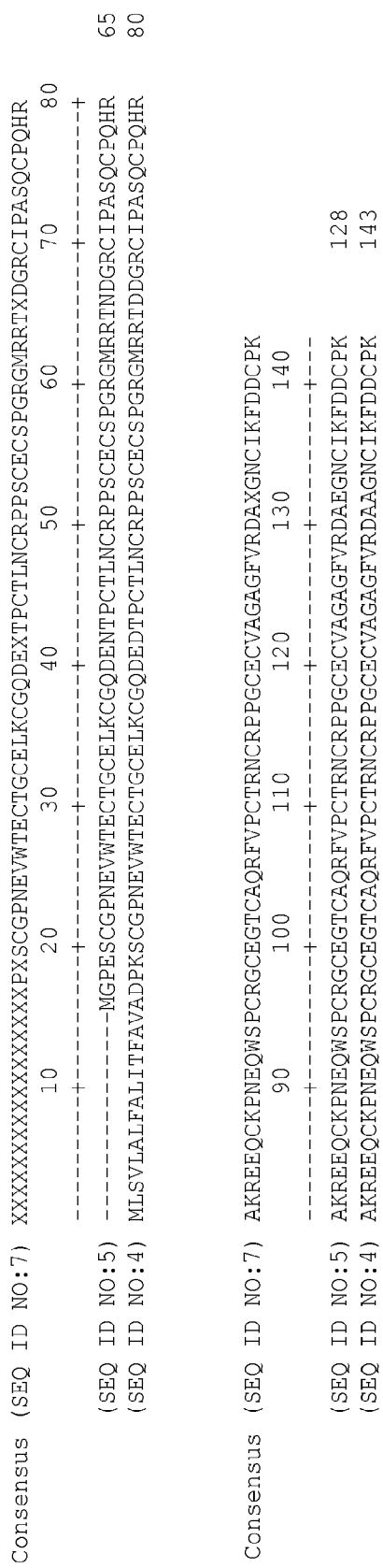
FIG. 5 shows a comparison alignment of SEQ ID NO:4 and SEQ ID NO:5. The consensus sequence of SEQ ID NO:4 and SEQ ID NO:5 is shown as SEQ ID NO:7.

The present invention is generally directed to methods, devices, kits and compositions for detecting roundworm in a sample obtained from a mammal. The present invention relates to roundworm antigens from *Toxocara*, such as *Toxocara canis* or *Toxocara cati*, for example. In particular, the present invention relates to *Toxocara* polypeptides and conservative variants thereof, polynucleotides that encode those polypeptides and oligonucleotides that specifically bind to those polynucleotides, antibodies that are raised against and that specifically bind those polypeptides, and methods, devices and kits for detecting roundworm, such as *Toxocara, Toxascaris, Baylisascaris, Ascaridia, Parascaris, Ascaris, Anisakis*, or *Pseudoterranova*, including *T. canis, T. cati, T vitulorum, T. leonina, B. procyonis, A. galli, P. equorum, A. lumbricoides, A. suum, A. simplex*, or *P. decipiens*, for example.

The present invention provides a superior alternative to the existing microscopic inspection techniques. This is true because the present invention provides devices, kits and methods for detecting the presence or absence of roundworm in a sample from a mammal that: (1) are both easy to use and yield consistently reliable results; (2) allow for the absence or presence of roundworm in a mammal to be confirmed regardless of whether that mammal is infected with hookworm, whipworm, and/or heartworm; (3) can detect roundworm prior to the time that the ova first appear in the infected host's feces; and (4) can distinguish between roundworm and other helminth infections.

The present invention is based in part on the discovery of an unexpected property of compositions of the present invention. Specifically, it was determined that an antibody of the present invention raised against a polypeptide of the present invention can be used to capture and detect roundworm antigens in a mammal, even when the mammal is also infested by one or more of hookworm, whipworm and heartworm. This specificity for roundworm is surprising because roundworms, whipworms, hookworms and heartworms all are related nematodes, and an antibody raised against a protein isolated from any one of these worms would be expected to crossreact with one or more of the other worms, host antigens, or other host components.

The present invention therefore includes methods, devices, compositions and kits that use antibodies and/or fragments thereof to specifically capture and detect roundworm coproantigens in a mammal that may also be infested by one or more of whipworm, hookworm and heartworm. The ability of the present invention to detect and diagnose roundworm even when one or more other worm types are also present allows the mammal's caregiver the opportunity to optimally select a treatment for ridding the roundworm from the mammal.

II. Definitions and Uses of Term

The term "compositions of the invention" refers to all of the nucleic acids, polypeptides, antibodies, and mixtures that include one or more of those nucleic acids, polypeptides, and antibodies and one or more other compounds, that can be used to detect the presence or absence of roundworm in a sample obtained from a mammal by carrying out the method of the present invention that are explicitly described, implicitly encompassed or otherwise disclosed herein.

"A sample from a mammal" in which roundworm can be detected by the present invention includes all bodily components and extracts thereof, such as any fluid, solid, cell or tissue, that are capable of containing roundworm antigen. Exemplary samples therefore include, but are not limited to being, feces, milk, whole blood and portions thereof, including serum, and further include tissue extracts, including tissue from mammary gland, intestine, liver, heart, lung, esophagus, brain, muscle, and eye, for example. The sample may be taken directly from the mammal or the sample may be taken from anything that has contacted the mammal. For example, the sample may be fresh or decaying fecal droppings from the mammal. As another example, the sample may include soil, dirt, sand, plant material, or any other material that may be mixed with bodily components that may be left behind by a mammal, such as feces, for example. No matter the origin or the content of the sample, this sample sometimes is referred to herein as the "mammalian sample", the "test sample" or the "sample under test".

As used herein, "nucleic acid" is synonymous with, and therefore is used interchangeably with, "gene", "DNA", "cDNA", "EST", "polynucleotide", "oligonucleotide", "polynucleic acid", "RNA" and "mRNA". A nucleic acid may be in double-stranded form or it may be in single-stranded form. Further, a nucleic acid is either naturally isolated, such as from a whole roundworm or a portion thereof, for example, or it is artificially synthesized, either in a recombinant host organism or by any other artificial means known to the skilled artisan, such as by employing a PCR-based technique, by creating a transgenic organism that synthesizes the nucleic acid, by using a DNA synthesizing machine, or by any another molecular-based technique, for example.

"Polypeptide", "peptide" and "protein" are synonymous terms that are used interchangeably herein to refer to a polymer of amino acid residues. A polypeptide, peptide and protein of the present invention may be either naturally isolated, such as from a whole roundworm or from a portion of roundworm, for example, or artificially synthesized, either in a recombinant host organism or by any other artificial means known to the skilled artisan.

The term "antibody" or "antibody of the present invention" refers to any antibody that is able to specifically bind to one or more roundworm antigens, but not to any antigen from hookworm, whipworm or heartworm. The antibodies of the present invention may be raised against one or more immunogenic polypeptides of the present invention. Unless otherwise stated, it is to be understood that the antibody of the present invention may include a mixture of two or more different types of antibody. For example, the antibody may be a mixture of two types of antibodies, wherein one of the two types specifically binds to one particular antigen and the other of the two types specifically binds to some other antigen.

The "immunogenic polypeptide of the present invention" and, more simply, "the polypeptide of the present invention", is an immunogen against which the antibodies of the present invention may be raised. All "polypeptides of the present invention" are immunogenic and therefore may be used to elicit an immune response in a host animal to produce the antibodies of the present invention. Unless otherwise stated, it is to be understood that the polypeptide of the present invention may be one component of a mixed composition of a plurality of components.

An "immunogen" is any agent, such as the immunogenic polypeptide of the present invention, for example, that is capable of eliciting an immune response in an animal that is exposed to that agent.

The term "roundworm", as used herein, refers to helminths such as intestinal roundworms of the order *Ascaridida*, which includes the genera *Toxocara, Toxascaris, Baylisascaris, Ascaridia, Parascaris, Ascaris, Anisakis*, and *Pseudoterranova*. Thus, the term "roundworm", as used herein, does not refer to the entirety of the phylum Nematoda. Therefore, "roundworm" does not include any member of the genera *Ancylostoma, Uncinaria, Necator, Trichuris* or *Dirofilaria*.

A "roundworm coproantigen" or a "coproantigen of roundworm" is any roundworm product that is present in the feces of a mammal having a roundworm infection and that may be specifically bound by one or more of the antibodies of the invention. For example, a roundworm coproantigen may be, but is not limited to being, one or more of the polypeptides of the invention The present inventors have determined that a novel C-terminal 7 kD isoform of DIV6728, which is a excretory/secretory protein of *T. canis*, is present in feces of *T. canis*-infected canines as early as 38 days after the canines first became infected with the *T. canis*. Therefore, a "roundworm coproantigen" may be this novel C-terminal 7 kD isoform of DIV6728 (which is referred to herein as "Copro6728") that has been observed in canine feces by the present inventors.

"Specific for", "specifically binds", and "stably binds" means that a particular composition of the invention, such as an antibody, polypeptide, or oligonucleotide of the present invention, for example, recognizes and binds to one or more other agents with greater affinity than to at least one other agent. As one example, an antibody of the present invention is said to be "specific for", to "specifically bind", and to "stably bind" roundworm antigens whenever that antibody is able to recognize and bind to those roundworm antigens with greater affinity than to any other antigens from a non-roundworm parasitic worm. Such binding specificity can be tested using methodology well known in the art, for example, ELISA or a radioimmunoassay (RIA). Based on information observed regarding the binding specificity of a particular composition of the invention, the method of the present invention can be carried out under conditions that allow that composition to bind to (and therefore to allow the detection of such binding to) a particular agent or agents, but not to significantly bind other agents, while those conditions are maintained. As one example, the method of the present invention can be carried out under conditions that allow an antibody of the present invention to bind to (and therefore to allow the detection of such binding to) one or more roundworm antigens present in a particular sample, but not significantly to any hookworm, whipworm or heartworm antigen that may be present in that sample.

"Detecting roundworm" means detecting one or more roundworm-specific products, including one or more of the polypeptides, antibodies and nucleic acids of the present invention, or one or more roundworm antigens, or Copro6728, for example. The presence of one or more such roundworm products in a sample from a mammal is indicative that the mammal has a roundworm infection, regardless of whether any whole roundworm organism or ovum thereof is also present in that sample. Conversely, the absence of one or more such roundworm products a sample from a mammal is indicative that the mammal does not have a roundworm infection.

"Amino acid" refers to naturally occurring and synthetic amino acids. Amino acid residues are abbreviated as follows: Alanine is A or Ala; Arginine is R or Arg; Asparagine is N or Asn; Aspartic Acid is D or Asp; Cysteine is C or Cys; Glutamic Acid is E or Glu; Glutamine is Q or Gln; Glycine is G or Gly; Histidine is H or His; Isoleucine is I or Ile; Leucine is L or Leu; Lysine is K or Lys; Methionine is M or Met; Phenylalanine is F or Phe; Proline is P or Pro; Serine is S or Ser; Threonine is T or Thr; Tryptophan is W or Trp; Tyrosine is Y or Tyr; and Valine is V or Val. Except where defined otherwise herein, X or Xaa represents any amino acid. Other relevant amino acids include, but are not limited to being, 4-hydroxyproline and 5-hydroxylysine. In all cases, the amino acid sequence of a polypeptide described or otherwise referred to herein is presented in conventional form in that the left-most, or first, amino acid residue of the sequence is the N-terminal residue and the right-most, or last, amino acid residue of the sequence is the C-terminal residue.

A "conservative variant" of any particular nucleic acid sequence includes any sequence having one or more degenerate codon substitutions to that particular nucleic acid sequence, any sequence having one or more nucleotide substitutions to, insertions to, and deletions from that particular nucleic acid sequence, and the complementary sequence of that particular nucleic acid and the conservative variants of that complementary sequence. Conservative variants of a particular nucleic acid sequence preferably have at least about 85% identity, more preferably have at least about 90% identity, and even more preferably at least about 95-99% identity, to that particular nucleic acid sequence. Conservative variants of a particular nucleic acid sequence may be artificially synthesized or they may be isolated in their natural form from an organism, including from a roundworm organism, such as *Toxocara canis* and *Toxocara cati*, for example.

A "conservative variant" of any particular polypeptide sequence is any polypeptide having an amino acid sequence that varies from the amino acid sequence of that particular polypeptide but still retains the specific binding properties of that particular polypeptide, such that an antibody of the present invention that is raised against the particular polypeptide is capable of specifically binding the variant polypeptide. Therefore, for example, a conservative variant of a particular polypeptide may have one or more amino acid substitutions, deletions, additions, and insertions to that particular polypeptide. For example, a conserved variant of a particular polypeptide may have 30 or fewer, 25 or fewer, 20 or fewer, 15 or fewer, 10 or fewer, or 5 or fewer, conserved amino acid substitutions to that particular polypeptide. Conservative variants of a particular polypeptide preferably, but not essentially, have at least about 80% identity, more preferably have at least about 90% identity, and even more preferably at least about 91-99% identity, to that particular polypeptide. A percent identity for any subject nucleic acid or amino acid sequence (e.g., any of polypeptides described herein) relative to another "target" nucleic acid or amino acid sequence can be determined as follows. First, a target nucleic acid or amino acid sequence of the invention can be compared and aligned to a subject nucleic acid or amino acid sequence, using the BLAST 2 Sequences (Bl2seq) program from the stand-alone version of BLASTZ containing BLASTN and BLASTP (e.g., version 2.0.14). The stand-alone version of BLASTZ can be obtained at www.ncbi.nlm.nih.gov. Instructions explaining how to use BLASTZ, and specifically the Bl2seq program, can be found in the 'readme' file accompanying BLASTZ. The programs also are described in detail by Karlin et al. (1990) Proc. Natl. Acad. Sci. 87:2264; Karlin et al. (1990) Proc. Natl. Acad. Sci. 90:5873; and Altschul et al. (1997) Nucl. Acids Res. 25:3389.

"Copro6728" refers to a C-terminal 7 kD portion of DIV6728 found in mammalian feces. In a specific embodiment, copro6728 does not include the C-terminus of the full length DIV6728.

Bl2seq performs a comparison between the subject sequence and a target sequence using either the BLASTN (used to compare nucleic acid sequences) or BLASTP (used to compare amino acid sequences) algorithm. Typically, the default parameters of a BLOSUM62 scoring matrix, gap existence cost of 11 and extension cost of 1, a word size of 3, an expect value of 10, a per residue cost of 1 and a lambda ratio of 0.85 are used when performing amino acid sequence alignments. The output file contains aligned regions, of homology between the target sequence and the subject sequence. Once aligned, a length is determined by counting the number of consecutive nucleotides or amino acid residues (i.e., excluding gaps) from the target sequence that align with sequence from the subject sequence starting with any matched position and ending with any other matched position. A matched position is any position where an identical nucleotide or amino acid residue is present in both the target and subject sequence. Gaps of one or more residues can be inserted into a target or subject sequence to maximize sequence alignments between structurally conserved domains (e.g., α-helices, β-sheets, and loops).

The percent identity over a particular length is determined by counting the number of matched positions over that particular length, dividing that number by the length and multiplying the resulting value by 100. For example, if (i) a 500 amino acid target sequence is compared to a subject amino acid sequence, (ii) the Bl2seq program presents 200 amino acids from the target sequence aligned with a region of the subject sequence where the first and last amino acids of that 200 amino acid region are matches, and (iii) the number of matches over those 200 aligned amino acids is 180, then the 500 amino acid target sequence contains a length of 200 and a sequence identity over that length of 90% (i.e., 180/200× 100=90). It will be appreciated that a nucleic acid or amino acid target sequence that aligns with a subject sequence can result in many different lengths with each length having its own percent identity. It is noted that the percent identity value can be rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

Conservative variants of a particular polypeptide sequence may be artificially synthesized or they may be isolated in their natural form from an organism, including from a roundworm organism, such as *Toxocara canis* and *Toxocara cati*, for example. In one specific example, the polypeptide of the invention having an amino acid sequence corresponding to SEQ ID NO:4 shown below is a conservative variant of the polypeptide of the present invention having an amino acid sequence corresponding to SEQ ID NO:3 in that SEQ ID NO:4 is more than 96% identical to SEQ ID NO:3 over an alignment of 128 amino acids. More generally, each one of SEQ ID NO:3, SEQ ID NO:4, SEQ ID NO:5, SEQ ID NO:6 and SEQ ID NO:7 are conserved variants of each other. It is also to be understood that other conserved variants of the SEQ ID NO:3, SEQ ID NO:4, SEQ ID NO:5, SEQ ID NO:6, SEQ ID NO:7 and SEQ ID NO:11 are contemplated by the present invention as described herein, but the skilled artisan would recognize that all of these contemplated variants are too numerous to list. The skilled artisan will also recognize that these variants include, but are not limited to, those have one or more substitutions of basic amino acid residues, one or more substitutions of acidic amino acid residues, one or more substitutions of polar amino acid residues, one or more substitutions of hydrophobic amino acid residues, one or more substitutions of aromatic amino acid residues, and one or more substitutions of small amino acid residues. ("Basic" amino acid residues are K, R and H. "Acidic" amino acid residues are D and E. "Polar" amino acid residues are N and Q. "Hydrophobic" amino acids are I, L, and V. "Aromatic" amino acid residues are F, Y, and W. "Small" amino acids are G, S, A, T and M.)

A. Nucleic Acids and Polypeptides of the Invention

A portion of the nucleic acids and polypeptides of the invention are described in detail in Provisional Application: "Methods, Devices, Kits And Compositions For Detecting Roundworm," Application Ser. No. 61/128,099, filed May 19, 2008, which is incorporated by reference in its entirety.

In an attempt to identify compositions that may be used to confirm the presence or absence of roundworm in a fecal sample, a plurality of oligonucleotide primers were designed, synthesized and used in 5' RACE, 3'RACE and RT-PCR reactions that included total RNA isolated from either whole adult *Toxocara canis* or whole adult *Toxocara cati*. As a result of these efforts, an 535-nucleotide cDNA sequence was deduced from *Toxocara canis* (this sequence is shown in FIG. 1 and is identified herein as SEQ ID NO:1), and a 536-nucleotide cDNA sequence was deduced from *Toxocara cati* (this sequence is shown in FIG. 2 and is identified herein as SEQ ID NO:2). (BLAST searches that were carried out using SEQ ID NO:1 and SEQ ID NO:2 indicated these sequences are likely to encode a member of a particular serine protease inhibitor family that was first identified in *Ascaris*, but that has not been identified in either *T. canis* or *T. cati* until now.)

Analysis of the sequences corresponding to SEQ ID NO:1 and SEQ ID NO:2 indicated that each one of these sequences contains a large open reading frame (ORF). Specifically, as shown in FIG. 3, the large ORF of SEQ ID NO:1 corresponds to nucleotides 28 through 456 of SEQ ID NO:1 and is predicted to encode a polypeptide having the following amino acid sequence:

(SEQ ID NO: 3)
MLSVLALFALITFAVAGPESCGPNEVWTECTGCELKCGQDENTPCTLNCR

PPSCECSPGRGMRRTNDGRCIPASQCPQHRAKREEQCKPNEQWSPCRGCE

GTCAQRFVPCTRNCRPPGCECVAGAGFVRDAEGNCIKFDDCPK.

Further, as shown in FIG. 4, the large ORF of SEQ ID NO:2 corresponds to nucleotides 29 through 457 of SEQ ID NO:2 and is predicted to encode a polypeptide having the following amino acid sequence:

(SEQ ID NO: 4)
MLSVLALFALITFAVADPKSCGPNEVWTECTGCELKCGQDEDTPCTLNCR

PPSCECSPGRGMRRTDDGRCIPASQCPQHRAKREEQCKPNEQWSPCRGCE

GTCAQRFVPCTRNCRPPGCECVAGAGFVRDAAGNCIKFDDCPK.

The polypeptides of the present invention are encoded for by nucleic acids that have a nucleotide sequence that corresponds to all or portions of SEQ ID NO:1 and SEQ ID NO:2 and all conservative variants of those sequences. It is to be understood therefore that the amino acid sequence of the polypeptide of the present invention is variable.

For example, the polypeptide of the present invention may have an amino acid sequence that corresponds to all or a portion of SEQ ID NO:3 or SEQ ID NO:4 or all or a portion of a conservative variant of SEQ ID NO:3 or SEQ ID NO:4.

In one specific example, the polypeptide of the present invention has the following amino acid sequence:

(SEQ ID NO: 5)
MGPESCGPNEVWTECTGCELKCGQDENTPCTLNCRPPSCECSPGRGMRRT

NDGRCIPASQCPQHRAKREEQCKPNEQWSPCRGCEGTCAQRFVPCTRNCR

PPGCECVAGAGFVRDAEGNCIKFDDCPK.

With 128 amino acids, protein DIV6728 (SEQ ID NO; 5) is about 14 kD in size and has a theoretical pI of about 6.54. This protein belongs to TIL superfamily, which is a group of serine protease inhibitors. In an effort to identify tools for capturing and detecting roundworm and/or roundworm antigen in roundworm-infected mammals, the present inventors have determined that only a truncated portion (about 7 kDa) of the full-length (14 kDa) protein, and therefore not the 14 kDa version, is present in the feces of canines that are infected by *T. canis*. (This 7 kDa truncated portion of DIV6728 is referred to herein as "Copro6728"; the detection of Copro6728 in feces of *T. canis*-infected canines is described in the Example section included herein.) In one aspect, therefore, the present invention provides polypeptides that may be used to generate antibodies that may be used to specifically capture and detect Copro6728.

The 127 amino acid residues that follow the N-terminal methionine residue of the polypeptide corresponding to SEQ ID NO:5 (DIV6728) specifically represent the amino acid residues 17 through 143 of SEQ ID NO:3. As described in the Example section included herein, the N-terminal methionine was artificially added to the N-terminus of this polypeptide by carrying out a standard cloning technique. Also as described throughout the Example section, antibody raised against the polypeptide corresponding to SEQ ID NO:5 was useful for detecting roundworm antigen. Because the N-terminal methionine was artificially added, and is not thought to naturally exist in *Toxocara* (the residue that is immediately prior to the glycine residue at position 17 in each one of SEQ ID NO:3 and SEQ ID NO:4 is alanine, and not methionine), it is therefore contemplated that the polypeptide of the present invention may have an amino acid sequence that corresponds to amino acid residues 17 through 143 of SEQ ID NO:3, or, more specifically:

(SEQ ID NO: 6)
GPESCGPNEVWTECTGCELKCGQDENTPCTLNCRPPSCECSPGRGMRRTN

DGRCIPASQCPQHRAKREEQCKPNEQWSPCRGCEGTCAQRFVPCTRNCRP

PGCECVAGAGFVRDAEGNCIKFDDCPK.

Further, an alignment of SEQ ID NO:5 (mostly *Toxocara canis*-derived sequence; with the only exception being the N-terminal methionine residue) to SEQ ID NO:4 (*Toxocara cati*-derived sequence) is shown in FIG. 5. Because antibody raised against a polypeptide having sequence corresponding to SEQ ID NO:5 was useful for detecting *Toxocara cati* (see the Example section included herein), it is additionally contemplated that the polypeptide of the present invention may have the amino acid sequence corresponding to SEQ ID NO:7 (which also is shown in FIG. 5), wherein the X at position 1 is absent or M, the X at position 2 is absent or L, the X at position 3 is absent or S, the X at position 4 is absent or V, the X at position 5 is absent or L, the X at position 6 is absent or A, the X at position 7 is absent or L, the X at position 8 is absent or F, the X at position 9 is absent or A, the X at position 10 is absent or L, the X at position 11 is absent or I, the X at position 12 is absent or T, the X at position 13 is absent or F, the X at position 14 is absent or A, the X at position 15 is absent or V, the X at position 16 is M or A, the X at position 17 is G or D, the X at position 19 is E or K, the X at position 42 is N or D, the X at position 66 is N or D, and the X at position 132 is E or A.

The polypeptide of the present invention may have the amino acid sequence corresponding to SEQ ID NO:11, wherein the amino acid at position 54 is E or A. Antibodies that specifically bind to this polypeptide are included in the invention.

It is also contemplated that any one or more of the SEQ ID NO:3, SEQ ID NO:4, SEQ ID NO:5, SEQ ID NO:6 and SEQ ID NO:7 may be only a portion of a larger polypeptide sequence, and therefore may represent partial sequence of one or more proteins that normally are expressed in roundworm, for example, or one or more polypeptide sequences that are artificially fused to SEQ ID NO:3, SEQ ID NO:4, SEQ ID NO:5, SEQ ID NO:6, SEQ ID NO:7, or SEQ ID NO:11, or Copro6728. The skilled artisan will recognize that are a variety of techniques exist for artificially fusing two or more polypeptide fragments together.

It is even further contemplated that the polypeptide of the present invention may include more than one of the SEQ ID NO:3, SEQ ID NO:4, SEQ ID NO:5, SEQ ID NO:6 SEQ ID NO:7, and SEQ ID NO:11, or Copro6728. For example, the polypeptide of the present invention may include the SEQ ID NO:5 fused to the SEQ ID NO:7. Also, it is contemplated that the polypeptide of the present invention may include a plurality of polypeptide fragments corresponding to SEQ ID NO:3, SEQ ID NO:4, SEQ ID NO:5, SEQ ID NO:6 SEQ ID NO:7, or SEQ ID NO:11, or Copro6728. For example, the polypeptide of the present invention may be formed by a plurality of polypeptide fragments corresponding to SEQ ID NO:5 that are fused together. In another example, the polypeptide of the present invention may be formed by a plurality of polypeptide fragments corresponding to SEQ ID NO:5 and a plurality of polypeptide fragments corresponding to SEQ ID NO:7 that are fused together in any combination.

Whereas one particular polypeptide of the present invention was expressed and isolated by a specific technique (in which is described in the Example section included herein), the skilled artisan will recognize that any of the polypeptides of the present invention may be isolated by employing any one or more of a variety of techniques. (See, e.g., Sewald and Jakubke, *Peptides: Chemistry and Biology*, Wiley Publishing (2002); *Peptide Synthesis and Applications (Methods in Molecular Biology)* Howl, ed., Humana Press (2005); Jones, *Amino Acid and Peptide Synthesis*, Oxford University Press (2002), each one of which is incorporated herein by reference in its entirety.) These techniques include those that may be carried out to isolate naturally existing polypeptides such as Copro6728, or polypeptides having amino acid sequence corresponding to SEQ ID NO:3, SEQ ID NO:4, SEQ ID NO:5, SEQ ID NO:6 SEQ ID NO:7, and SEQ ID NO:11, and any naturally occurring variant of those polypeptides. These techniques further include those that may be carried out to artificially generate the polypeptides having amino acid sequence corresponding to SEQ ID NO:3, SEQ ID NO:4, SEQ ID NO:5, SEQ ID NO:6 SEQ ID NO:7, and SEQ ID NO:11 and any conserved variant of those polypeptides. Such variants may be generated, for example, by employing any one or more mutagenesis techniques or by direct synthesis.

The polypeptides of the present invention are capable of eliciting an immune response in a host animal that is exposed to these polypeptides to produce one or more of the antibodies of the present invention. Regardless of the technique by which they are derived, the polypeptides of the present invention are preferably prepared in substantially pure form when they are to be used for the purpose of raising antibody. Preferably, these polypeptides are at least about 80% pure, more preferably are at least about 90-95% pure, and even more preferably are at least about 99% pure. Exemplary techniques for eliciting an immune response in a host organism and for isolating antibodies therefrom are described herein, but it is to be understood that the present invention is not limited to those techniques. The skilled artisan will recognize that there are a plurality of techniques for achieving this same goal without deviating from the scope and spirit of the invention.

B. Antibodies of the Invention

The present invention further includes antibodies and antigen-binding fragments thereof that are raised against and that specifically bind all or part of one or more polypeptides of the present invention, and also includes compositions that include said antibodies and antigen-binding fragments thereof. When contacted to a sample obtained from a mammal, these antibodies and antigen-binding fragments are able to specifically bind roundworm antigen present in the sample, but are not able to specifically bind any antigen from hookworm, whipworm, or heartworm that may be present in the sample. The antibodies of the present invention are suitable for being used only to capture one or more roundworm antigens, only to detect one or more roundworm antigens, or more preferably, to both capture and detect one or more roundworm antigens.

The antibodies of the present invention may belong to any antibody class, including for example, IgG, IgM, IgA, IgD and IgE, and may be prepared by any of a variety of techniques known to the skilled artisan. (See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992); Harlow and Lane, *Antibodies: A Laboratory Manual*, Cold Spring Harbor Laboratory (1988); and *Making and Using Antibodies: A Practical Handbook*, Howard and Kaser, eds., CRC Press (2006), each one of which is incorporated herein by reference in its entirety.)

In one technique, the polypeptide of the invention is introduced into a host animal, such as into rabbit, mouse, rat, guinea pig, goat, pig, cow, sheep, donkey, dog, cat, chicken, or horse, for example. An enhanced immune response may be elicited in the host animal by associating the polypeptide with a carrier and/or by exposing the host to an adjuvant, but it is to be understood that the present invention does not require that the polypeptide be associated with a carrier or that the host be exposed to the adjuvant. An exemplary carrier that may be used for this purpose is bovine serum albumin, bovine thyroglobulin, and soybean trypsin inhibitor. Exemplary adjuvants include Freund's complete or incomplete adjuvant and MDL-TDM adjuvant. Regardless of whether the polypeptide is associated with such a carrier or whether the host is exposed to an adjuvant, booster immunizations optionally may be made with the host animal being bled one or more times thereafter. Polyclonal antibodies that specifically bind the polypeptide may then be purified from antisera obtained from the bleed or bleeds. Such purification may be achieved, for example, by employing affinity chromatography techniques that involve associating the polypeptide to a solid support. Such affinity chromatography techniques are well known by the skilled artisan.

In one embodiment, the antibody of the present invention is an antibody that is raised in rabbit by immunizing that host animal with the polypeptide having the amino acid sequence corresponding to SEQ ID NO:5. (Hereinafter, this particular antibody is referred to as "anti-DIV6728 pAB".) A specific technique for producing and isolating anti-DIV6728 pAB is described in the Example section included herein, but the skilled artisan will recognize that the production and isolating of anti-DIV6728 pAB, or any other antibody of the present invention, is not limited to that specific technique.

In another embodiment, the antibody of the present invention is an antibody that is raised in rabbit by immunizing that host animal with a polypeptide having the amino acid sequence corresponding to SEQ ID NO:11. (Hereinafter, this particular antibody is referred to an "anti-6728C".) A specific technique for producing and isolating this antibody is described in the Example section herein, but the skilled artisan will recognize that the production and isolating of anti-Copro6728C is not limited to that specific technique.

In other embodiments, the antibody of the present invention is raised in a host against one or more polypeptides having an amino acid sequence that is a conservative variant of the sequence corresponding to SEQ ID NO:5. In some other embodiments, the antibody of the present invention is raised in a host against any one or more polypeptides having an amino acid sequence corresponding to the sequence of SEQ ID NO:3, SEQ ID NO:4, SEQ ID NO:6, or SEQ ID NO:7, or one or more polypeptides having an amino acid sequence that is a conservative variant of any of those sequences.

In another embodiment, the antibody of the present invention is an antibody that specifically binds Copro6728 and/or one or more the polypeptide having the amino acid sequence corresponding to SEQ ID NO:3, SEQ ID NO:4, SEQ ID NO:5, SEQ ID NO:6, SEQ ID NO:7 or SEQ ID NO:11, or antigenic portions thereof.

In yet other embodiments, the antibody of the present invention specifically binds one or more polypeptides having an amino acid sequence that is a conservative variant of Copro6728, or of the sequence corresponding to SEQ ID NO:5 or SEQ ID NO:11. In some other embodiments, the antibody of the present invention specifically binds one or more polypeptides having an amino acid sequence corresponding to the sequence of SEQ ID NO:3, SEQ ID NO:4, SEQ ID NO:6, or SEQ ID NO:7, or one or more polypeptides having an amino acid sequence that is a conservative variant of any of those sequences.

It is also to be understood that the antibodies of the invention optionally may be polyclonal or monoclonal antibodies, single chain antibodies (scFv), chimeric antibodies, and fragments thereof. Monoclonal antibodies that are specific for the polypeptide of interest may be obtained and purified, for example, by preparing cell lines that generate antibodies having the desired specificity to the polypeptide of interest. Cell lines of this kind may be derived from cells of a particular type (e.g., spleen cells) that are isolated from a host animal that had previously been immunized with the polypeptide as described before. In such a case, these cells could then be immortalized, for example, by fusing them with myeloma cells by carrying out any one of a variety of fusion techniques known to the skilled artisan. In one exemplary technique, the cells from the immunized host animal are co-incubated with their fusion partner, e.g., the myeloma cells, in the presence of a detergent for a short period of time before being plated on a medium that supports the growth of hybrid cells (but not the myeloma fusion partner). Such selection may be achieved, for example, by using hypoxanthine, aminopterin, and thymidine (HAT). When hybrid cells emerge during selection, in perhaps one or two weeks after commencing the selection process, single hybrid colonies (and their supernatants) are tested for their ability to bind the polypeptide or polypeptides against which the host animal was immunized. Hybrid colonies having the most optimal binding specificity would represent the best candidates from which monoclonal antibodies may be isolated. These monoclonal antibodies, for example, may be isolated directly from the supernatant (i.e., medium) in which these colonies are grown by employing any one of a variety techniques known to the skilled artisan.

The antibodies of the invention also may be a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F$_v$ fragments. In addition to production and purification from animals or mammalian cells, antibodies, antibody fragments, or non-antibody scaffolds can be selected based upon various in vitro technologies, including phage display, ribosomal display, or bacterial display.

Antibodies, including secondary antibodies, may be labeled with any type of label known in the art, including, for example, fluorescent, chemiluminescent, radioactive, enzymes, colloidal particles, radioisotopes and bioluminescent labels. In various embodiments of the invention, the one or more of the antibodies of the invention are labeled with an enzyme, a colloidal particle, a radionuclide or a fluorophor. The particulate label can be, for example, a colored latex particle, dye sol, or gold sol conjugated to an antibody.

C. Methods, Devices and Kits of the Invention

1. Devices and Kits of the Invention

The present invention, in one aspect, is a device for the detection of roundworm infection in a mammal, such as a canine, feline, porcine, bovine, or human, for example. The device is arranged to aid in the detection of the presence or absence of roundworm antigen in a sample from a mammal that may also be infected with one or more other worm parasites, including hookworm, whipworm, and heartworm.

In one aspect, the device includes a solid support, wherein one or more antibodies of the invention are immobilized on the solid support. The solid support may be, but is not limited to being, the inner, bottom surface of a well of a microtiter plate or a substrate that is included as part of a lateral flow device, for example. An exemplary microtiter plate is an Immulon 1B 96-well plate (which is commercially available from Thermo Scientific of Milford, Mass.), but it is to be understood that the skilled artisan will recognize that a large variety of other microtiter plates that are not the Immulon 1B 96-well plate allow for the immobilization of antibodies thereon, and therefore would be suitable for providing the solid support of the present invention.

An exemplary lateral flow device is the lateral flow device that is described in U.S. Pat. No. 5,726,010, which is incorporated herein by reference in its entirety. The device for performing a lateral flow assay may be a SNAP® device, which is commercially available from IDEXX Laboratories, Inc. of Westbrook, Me. However, it is to be understood that the skilled artisan will recognize that a large variety of other lateral flow devices that are not SNAP® devices or described by U.S. Pat. No. 5,726,010 allow for the immobilization of an antibody thereon, and therefore would be suitable for being used as the device of the present invention. These devices can include, for example, lateral flow devices that use colloidal gold technology.

Antibodies used in the device of the invention may be immobilized on the solid support by any methodology known in the art, including, for example, covalently or non-covalently, directly or indirectly, attaching the antibodies to the solid support. Therefore, while these antibodies may be attached to the solid support by physical adsorption (i.e., without the use of chemical linkers), it is also true that these antibodies may be immobilized to the solid support by any chemical binding (i.e., with the use of chemical linkers) method readily known to one of skill in the art.

It is also to be understood that the solid support may be any suitable material for the immobilization of the antibodies of the invention. For example, the solid support may be beads, particles, tubes, wells, probes, dipsticks, pipette tips, slides, fibers, membranes, papers, natural and modified celluloses, polyacrylamides, agaroses, glass, polypropylene, polyethylene, polystyrene, dextran, nylon, amylases, plastics, magnetite or any other suitable material readily known to one of skill in the art.

The device optionally may include one or more labeled antigen capture reagents that may be mixed with a sample from a mammal prior to application to a device of the invention. When the labeled capture antigen reagent is included, the labeled antigen capture reagent may or may not be deposited or dried on a solid surface of the device. "Antigen capture reagent" refers to any compound that is specific for the antigen or antigens of interest. The labeled antigen capture reagent, whether added to the mammalian sample or pre-deposited on the device, may be, for example, a labeled antibody specific for a roundworm antigen, including, but not limited to, the antibodies of the present invention. For instance, anti-DIV6728 or anti-Copro6728 conjugated with horseradish peroxidase may be used as a labeled antigen capture reagent.

The device also may optionally include a liquid reagent that transports (such as when the device is a SNAP® device, for example), or otherwise facilitates removal of (such as when the device includes a microtiter plate, for example), unbound material (e.g., unreacted portions of the mammalian sample, such as, for example, unreacted portions of fecal extract, and unbound antigen capture reagent) away from the reaction zone (solid phase). The liquid reagent may be a wash reagent and serve only to remove unbound material from the reaction zone, or it may include a detector reagent and serve to both remove unbound material and facilitate antigen detection. For example, in the case of an antigen capture reagent conjugated to an enzyme, the detector reagent includes a substrate that produces a detectable signal upon reaction with the enzyme-antibody conjugate at the reaction zone (solid phase). Alternatively, in the case of a labeled antigen capture reagent conjugated to a radioactive, fluorescent, or light-absorbing molecule, the liquid reagent acts merely as a wash solution facilitating detection of complex formation at the reactive zone by washing away unbound labeled reagent.

The liquid reagent may further include a limited quantity of an "inhibitor", i.e., a substance that blocks the development of the detectable end product. A limited quantity is defined as being an amount of inhibitor sufficient to block end product development until most or all excess, unbound material is transported away from the second region, at which time detectable end product is produced.

The device of the present invention may also include various binding reagents immobilized at locations distinct from the antigen capture reagent or reagents. For example, an immunoreagent (an antibody, antigen or polypeptide) that recognizes a species-specific (e.g., roundworm-specific) antibody portion of a labeled antibody or antigen capture reagent, or an enzyme portion of an enzyme-labeled reagent, can be included as a positive control to assess the viability of the reagents within the device. For example, a positive control may be an anti-horseradish peroxidase antibody that has been raised in, for example, goat or mouse. Additionally, a reagent, e.g., an antibody, isolated from a non-immune member of the species from which the antibody portion of the antigen-antibody complex was derived can be included as a negative control to assess the specificity of immunocomplex (i.e., antigen-antibody complex) formation.

In addition to being designed to detect roundworm in a mammalian sample, the device of the invention optionally may be designed to allow one or more other diagnostic tests to be performed. For example, the solid support may also include reagents for the detection of one or more non-roundworm worm parasites, one or more non-worm parasites, one or more viruses, one or more fungi, or one or more bacteria. The reagents for the detection of one or more non-roundworm worm parasites, one or more non-worm parasites, one or more viruses, one or more fungi, or one or more bacteria may be, for example, one or more antibodies or one or more antigens recognized by antibodies specific for one or more non-roundworm worm parasites, one or more non-worm parasites, one or more viruses, one or more fungi, or one or more bacteria.

Figure 6A:
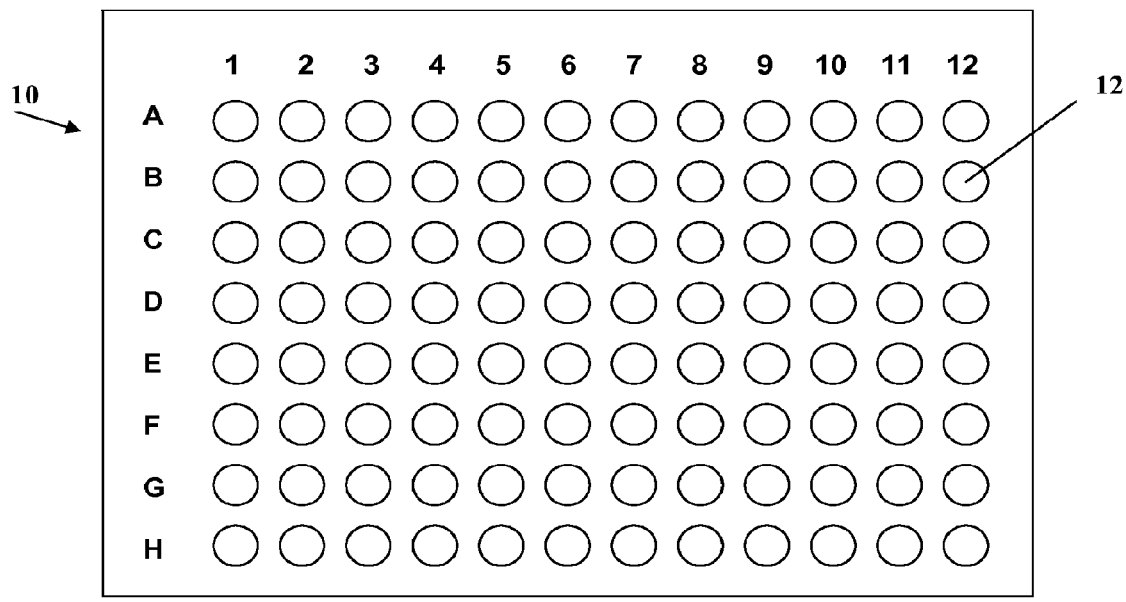
FIG. 6A shows a multi-well plate device of the present invention.
Figure 6B:
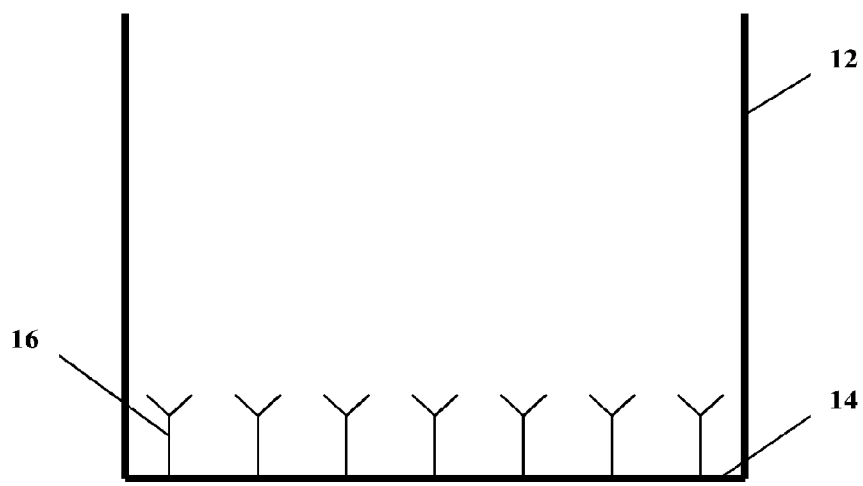
FIG. 6B shows a close up of a single well of the plate of FIG. 6A with a specific antibody of the present invention immobilized thereto.

In one embodiment, which is shown in FIGS. 6A and 6B, the device of the present invention is a microtiter plate 10 that includes a plurality of wells 12, wherein each well 12 includes a solid support 14 having anti-DIV6728 pAB (represented as element 16) immobilized thereupon.

The plate 10 may be used in conjunction with a method of the present invention to detect roundworm in a mammalian sample. Specifically, a roundworm infection may be diagnosed in a mammal by detecting one or more roundworm antigens with the anti-DIV6728 pAB that is immobilized on the solid support 14. In one embodiment, the antigens that are detected are roundworm coproantigens. "Roundworm coproantigens" are any product or products of roundworm that are present in a fecal sample and that can specifically and stably bind to the anti-DIV6728 pAB or anti-Copro6728 pAB. Roundworm coproantigens therefore may be whole roundworm, roundworm eggs, roundworm fragments, or products secreted, excreted or shed from roundworm or a combination thereof. Roundworm coproantigens further include the polypeptides of the present invention, such as Copro6728 and the polypeptides having an amino acid sequence corresponding to SEQ ID NO:3, SEQ ID NO:4, SEQ ID NO:5, SEQ ID NO:6, SEQ ID NO:7 or SEQ ID NO:11, polypeptides having an amino acid sequence that is a conservative variant of those sequences, and/or antigenic fragments of any such polypeptides, for example. An exemplary roundworm coproantigen is Copro6728 that was detected by the present invention in fecal samples obtained from roundworm-infected canines as described herein.

The invention further includes assay kits (e.g., articles of manufacture) for detecting roundworm in a mammalian sample. A kit therefore may include one or more devices and/or compositions of the present invention. For example, the kit may include anti-roundworm antibodies and means for determining binding of the antibodies to roundworm antigens in the sample. In one particular example, such a kit includes the device having an immobilized anti-roundworm antibody, such as anti-DIV6728 pAB or anti-Copro6728 pAB, for example, one or more antigen capture reagents (e.g., a non-immobilized labeled antigen capture reagent and an immobilized antigen capture reagent) and wash reagent, as well as detector reagent and positive and negative control reagents, if desired or appropriate. Other components such as buffers, controls, and the like, known to those of ordinary skill in art, may be included in such test kits. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample. The present kit may further include instructions for carrying out one or more methods of the present invention, including instructions for using any device and/or composition of the present invention that is included with the kit.

2. Methods of the Invention

The present invention further includes methods for using one or more of the devices, kits and/or compositions of the present invention to detect the presence or absence of roundworm in a sample. The methods therefore may be carried out to detect the presence or absence of roundworm in a sample, such as, for example, a fecal sample, that is obtained from a mammal, including, but not limited to, a canine, feline, porcine, bovine or human. Further, the methods may be carried out to detect *Toxocara*, such as *T. canis* or *T. cati*, or *T. vitulorum*, for example. It is to be understood, however, that these methods are not limited to being used to detect *Toxocara*, and therefore these methods may be carried out for the purpose of detecting other species of roundworm, such as *Toxascaris*, including *T. leonina*, *Baylisascaris*, including *B. procyonis*, *Ascaridia*, including *A. galli*, *Parascaris*, including *P. equorum*, *Ascaris*, including *A. lumbricoides* and *A. suum*, *Anisakis*, including *Anisakis simplex*, or *Pseudoterranova*, including *P. decipiens*, for example These methods further are useful for confirming such presence or absence of roundworm in a sample even when that sample includes one or more products derived from other worm species, including one or more products from hookworm, whipworm, and/or heartworm.

In the methods of the present invention, detection of roundworm may be accomplished by detecting the presence or absence of one or more roundworm antigens, such as Copro6728 or the polypeptides having an amino acid sequence corresponding to SEQ ID NO:3, SEQ ID NO:4, SEQ ID NO:5, SEQ ID NO:6, SEQ ID NO:7, or SEQ ID NO:11, as well as antigenic fragments and/or conservative variants of those sequences, for example. When the sample under test for roundworm is feces, the soluble portion of the feces may be collected by any protocol known in art. For example, in addition to the specific protocol described in the Example section herein, the soluble portions of the sample generally may be collected by using filtration, extraction, centrifugation, or simple mixing followed by gravimetric settling. The skilled artisan will recognize that there are a variety of ways of extracting and preparing non-fecal samples from a mammal as well. For example, the sample may be a bodily fluid that is naturally excreted or otherwise released by the mammal or that is artificially obtained from the mammal. Such artificial extraction may be carried out by milking the mammal or by injecting a syringe into the mammal and drawing the fluid into the syringe. Once obtained, the fluid optionally may be fractionated (for example, serum may be fractionated from whole blood as then used as the sample). As another example, the sample may be obtained by swabbing the mammal, such as the oral cavity of the mammal, for example. As yet another example, tissue sections may be obtained by biopsy.

The methods include contacting the mammalian sample with one or more antibodies specific for one or more roundworm antigens under conditions that allow an antigen/antibody complex, i.e., an immunocomplex, to form. That is, an antibody specifically binds to a roundworm antigen present in the sample. The skilled artisan is familiar with assays and conditions that may be used to detect such antigen/antibody complex binding. For example, the antigen/antibody complex may be detected using a secondary antibody that binds to the antigen/antibody complex. The formation of a complex between roundworm antigen and anti-roundworm antibodies in the sample may be detected using any suitable method known in the art.

Further, the relative amount of antibody-antigen complexes that are formed in one particular reaction may be measured with respect to those formed in any other reaction by any methodology known in the art for achieving that goal. When it is determined that a sample under test has more antibody-antigen complexes than does a control sample, it can be concluded that roundworm is present in the test sample. When this is true, it may be concluded that the mammal from which the test sample was obtained harbors an intestinal roundworm infection. Either one or both of the conclusions that roundworm is present in the test sample and that the mammal being tested harbors an intestinal roundworm infection may be made by a clinician at a diagnostic service provider or by a caregiver of the mammal, such as the mammal's veterinarian, for example. When a caregiver of a mammal determines (or is otherwise informed that) a mammal harbors a roundworm infection, the caregiver may then subject the mammal to a course of treatment that is optimally designed to rid the mammal of roundworm specifically, rather than of a parasitic nematode infection generally. In addition, humans who may come in contact with the infested animal or its excretions may be advised to take precautions against acquiring the parasite. In this context, it is important to determine the worm species with high specificity, as some helminths, such as roundworms and hookworms, can cause significant disease (e.g., larval migrans, severe enteritis, and allergic reactions) in humans, while it is generally accepted that whipworm does not play a zoonotic role of importance in humans. Further, the present invention can be used to confirm that any animal that has received treatment for a roundworm infection has been rid of that infection.

The steps of the method of the present invention may include applying a mammalian sample to a device of the invention, which includes an immobilized antibody specific for one or more roundworm antigens, and detecting the presence or absence of the roundworm antigen in the sample. Antibodies specific for antigens of roundworms may be directly or indirectly attached to a solid support or a substrate such as a microtiter well, antibody-immobilizing portion of a SNAP® device, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). All of these substrate materials may be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

The methods of the present invention do not require the use of solid phases or substrates, however. The skilled artisan will recognize that there are a number of ways that the present method may be carried out to detect the presence or absence of roundworm without involving the use of solid phases or substrates. In just one example, immunoprecipitation methods that do not require the use of solid phases or substrates may be carried out.

In some embodiments of the invention, the antigen/antibody complex is detected when an indicator reagent, such as an enzyme conjugate, which is bound to the antibody, catalyzes a detectable reaction. Optionally, an indicator reagent including a signal generating compound may be applied to the antigen/antibody complex under conditions that allow formation of a detectable antigen/antibody/indicator complex. Optionally, the antibody may be labeled with an indicator reagent prior to the formation of an antigen/antibody complex.

The formation of an antigen/antibody complex or an antigen/antibody/indicator complex in some of the methods of the present invention specifically may be detected by radiometric, colorimetric, fluorometric, photometric, size-separation, or precipitation methods. Detection of an antigen/antibody complex also may be accomplished by the addition of a secondary antibody that is coupled to an indicator reagent including a signal generating compound. Indicator reagents including signal generating compounds (labels) associated with a polypeptide/antibody complex may be detected using the methods described above and may include chromogenic agents, catalysts such as enzyme conjugates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Methods of the invention include, but are not limited to those based on competition, direct reaction or sandwich-type assays, including, but not limited to ELISA, RIA, immunofluorescent assays (IFA), hemagglutination (HA), fluorescence polarization immunoassay (FPIA), and microtiter plate assays (i.e., any assay done in one or more wells of a microtiter plate). One assay of the invention includes a reversible flow chromatographic binding assay, which may be performed, for example, by using a SNAP® device. See U.S. Pat. No. 5,726,010.

In some embodiments, the method of the invention facilitates sandwich or competition-type specific binding assays. In a sandwich assay, antigen capture reagents are immobilized in a reactive zone. These antigen capture reagents may specifically bind to antigens in the sample being tested for roundworm. Following binding of the antigen from the sample, the antigen capture reagent/antigen complex is detected by any suitable method. For example, the complex may be reacted with labeled specific binding reagents (e.g., an enzyme-antibody conjugate) and antigen detected (e.g., upon reaction with substrate).

In other embodiments of the method of the present invention, a competition assay is performed. In a competition assay, antigen capture reagents are immobilized at the reactive zone and are contacted simultaneously with antigen from a sample and labeled antigen (e.g., an antigen-enzyme conjugate). The amount of label detected at the reactive zone is inversely proportional to the amount of antigen in the sample.

In some embodiments of the method, antibodies specific for a roundworm antigen or antigens are attached to a solid phase or substrate. A sample potentially including an antigen from roundworm is added to the substrate. Antibodies that specifically bind roundworm are added. The antibodies may be the same antibodies used on the solid phase or they may be from a different source or species. Further, these antibodies may be linked to an indicator reagent, such as an enzyme conjugate. Wash steps may be performed prior to each addition. A chromophore or enzyme substrate may be added and color may be allowed to develop. The color reaction may be stopped and the color may be quantified using, for example, a spectrophotometer, and/or the color may be subjectively assessed by the human eye.

In other embodiments of the method, antibodies specific for a roundworm antigen or antigens are attached to a solid phase or substrate. A sample potentially including a roundworm antigen is added to the substrate. Second anti-species antibodies that specifically bind antigens of roundworms are added. These second antibodies are from a different species than are the solid phase antibodies. Third anti-species antibodies that specifically bind the second antibodies and that do not specifically bind the solid phase antibodies are added. The third antibodies may include an indicator reagent, such as an enzyme conjugate. Wash steps may be performed prior to each addition. A chromophore or enzyme substrate may added and color may be allowed to develop. The color reaction may be stopped and the color may be quantified using, for example, a spectrophotometer, and/or the color may be subjectively assessed by the human eye.

In a specific example, the method of the present invention is performed in conjunction with a device that is a lateral flow assay device by adding a prepared mammalian sample to a flow matrix of the device at a first region (a sample application zone). The prepared sample is carried in a fluid flow path by capillary action to a second region of the flow matrix where a particulate label capable of binding and forming a first complex with an antigen in the sample exists. The particulate label can be, e.g., a colored latex particle, dye sol, or gold sol conjugated to an antibody specific for a roundworm antigen. The first complex is carried to a third region of the flow matrix where an antibody that specifically binds a roundworm antigen is immobilized at a distinct location. A second complex is formed between the immobilized antibody and the first complex. The particulate label that is part of the second complex can be directly visualized by the human eye.

Roundworm antibody may be an immobilized antigen capture reagent in a reaction zone (solid phase). A second antigen capture reagent, i.e., a second roundworm antibody that has been conjugated to a label, either may be added to the sample before the sample is added to the device, or the second antigen capture reagent can be incorporated into the device. For example, the labeled antigen capture reagent may be deposited and dried on a fluid flow path that provides fluid communication between a sample application zone and the solid phase. Contact of the labeled antigen capture reagent with the test sample can result in dissolution of the labeled antigen capture reagent.

In one embodiment of the method of the present invention, roundworm antigen is detected by ELISA. Specific examples of the ELISA method of the present invention is described in the Example section included herein. Although the present invention is described with respect to those specific ELISA methods, however, it is to be understood that those of ordinary skill in the art will recognize that alternative, additional or substitute ELISA steps may be used without deviating from the basic goal achieved through this method of the invention.

In another embodiment of the present invention, roundworm antigen is detected by using a lateral flow device, such as a SNAP® device, for example.

Further, the methods of the invention for detection of roundworm infection can be combined with other diagnostic assays to detect the presence of other organisms or conditions. For example, assays of the invention can be combined with reagents that detect one or more non-roundworm worm fecal parasites, one or more non-worm fecal parasites, one or more viruses, one or more fungi, one or more bacteria, one or more blood-borne parasites or occult blood or a combination thereof. By providing two or more unique binding sites in a single assay device (such as, for example, two unique spots on a SNAP® assay device), the present invention allows for detection of two or more organisms from a single sample. In one embodiment, there are three unique spots for detection of past or present infection or infestation from three organisms (the spots being either antigen or antibody binding reagents) from a single sample (i.e., the same individual sample is exposed to the three capture reagents on a single device). In yet another embodiment, there are four unique spots for detection of past or present infection or infestation from four organisms (the spots being either antigen or antibody binding reagents) from a single sample (i.e., the same individual sample is exposed to the four capture reagents on a single device. It is to be understood, however, that the same device may include more than four unique spots and/or allow for the detection of more than four organisms.

The reagents for the detection of one or more non-roundworm worm parasites, one or more non-worm parasites, one or more viruses, one or more fungi, or one or more bacteria may be, for example, one or more antibodies or one or more antigens recognized by antibodies specific for one or more non-roundworm worm parasites, one or more non-worm parasites, one or more viruses, one or more fungi, or one or more bacteria.

When a device of the present invention includes reagents for the specific detection of hookworm and reagents for the specific detection whipworm, for example, in addition to the reagents for detecting roundworm, the method of the present invention may involve using that device for the additional purpose or purposes of determining whether the sample that is being tested for roundworm also includes hookworm and/or whipworm. In this arrangement, therefore, the method/device of the present invention would not only be able to specifically confirm that roundworm is present in or absent from any particular test sample, but it would also be useful for specifically confirming that the sample includes or does not include any antigen of hookworm and/or any antigen of whipworm. The capability to specifically detect roundworm and one or more other organisms by applying a single sample to the device of the invention would be useful to the caregiver of the animal from which the sample under test was obtained. A caregiver who learns that a sample includes both roundworm and whipworm, but not hookworm, for example, could use that knowledge to treat the mammal from which the sample was taken specifically for roundworm by administering to that mammal a drug optimally effective against roundworm and a second drug optimally effective against whipworm. Absent such knowledge, the caregiver may, for example, otherwise treat the mammal with a drug that is optimally effective against only roundworm, only whipworm, or neither roundworm nor whipworm (in such cases, the mammal would be at risk of receiving suboptimal treatment). In addition, humans who may come in contact with the infested animal or its excretions may be advised to take precautions against acquiring the parasite or parasites. In this context, it is important to determine the worm species with high specificity, as some helminths, such as roundworms and hookworms, can cause significant disease (e.g., larval migrans) in humans, while it is generally accepted that whipworm does not play a zoonotic role of importance in humans.

The method further may optionally include using one or more nucleic acids from roundworm, including, but not limited to, the nucleic acids of the present invention, to determine the presence or absence of roundworm in a mammalian sample. Such use of these nucleic acids for determining the presence of roundworm may be carried out before, after or concomitantly with the carrying out of any other aspects of the method, including the detection of roundworm by antibody. Therefore, in one aspect, after roundworm is detected or not detected in a particular sample and the mammal from which the sample was obtained is diagnosed as either having or not having a roundworm infection, the sample (or a later-obtained sample from the diagnosed mammal) may be tested for the presence or absence of any one or more of the nucleic acids, including any one or more nucleic acids of the invention. Anyone failing to detect roundworm in a particular mammal by using one or more nucleic acids (after the roundworm had been detected by using one or more antibodies) would need to take into consideration the possibility that the antibodies had detected roundworm antigen prior to the appearance of detectable roundworm nucleic acid in the sample. In such an instance, the mammal's caregiver may elect to ignore the observation that the nucleic acid had failed to detect the roundworm and proceed with treating the mammal specifically for roundworm infection based on the observation that the antibodies had in fact detected roundworm. In another aspect, the nucleic acids are used to determine the presence or absence of roundworm in a particular mammal, and then the presence or absence of roundworm is further evaluated by using the antibodies of the present invention. Detection of one or more roundworm nucleic acids may be carried out by using any nucleic acid detection techniques known to the skilled artisan. For example, such detection may be carried out by performing a PCR-based technique, such as, but limited to, for example, a real-time PCR-based technique. Exemplary PCR-based techniques are described in, e.g., *PCR Protocols (Methods in Molecular Biology)*, $2^{nd}$ ed., Bartlett and Stirling, eds., Humana Press (2003); and Sambrook and Russell, *Molecular Cloning: A Laboratory Manual*, Cold Spring Harbor Laboratory Press (2001); each one of which is incorporated herein by reference in its entirety.

The present invention is specifically described with reference to six Examples; however, it is not to be construed as being limited thereto.

EXAMPLES

Unless otherwise indicated, the following materials and techniques were used to generate data described in one or more of Examples 1-8 as described below.

Polyclonal antibody preparation. The polyclonal antibody "anti-DIV6728 pAB" (IgG) was raised in rabbit against a polypeptide having amino acid sequence corresponding to SEQ ID NO:5 and purified from serum by using standard methods. Briefly, nucleotides 76 through 456 of SEQ ID NO:1 were cloned in-frame into a vector (D8223, which is a derivative of pUC19) to create the plasmid D8245. Specifically, the 125 amino acids of SEQ ID NO:5 that follow the methionine residue at the N-terminus of that sequence correspond to a portion of SEQ ID NO:3 and are encoded for by the cloned portion of SEQ ID NO:1. In the D8245 plasmid, the N-terminal methionine residue was encoded for by vector sequence at the junction of that plasmid where the vector was ligated to the cloned sequence from SEQ ID NO:1.

DNA sequence encoding SEQ ID NO:5 was then cleaved from the D8245 plasmid by restriction exonuclease digestion (NdeI and BamHI) and purified. This purified sequence was then ligated to linearized expression vector, pET28a, and the resulting circular construct (pTDX198::DIV6728) was transformed into BL21 (DE3) *E. coli* cells. (The complete sequence of the insert was confirmed by DNA sequence analysis.) Expression of His-tagged fusion protein was induced by addition of 1 mM IPTG to cultures of the transformed *E. coli*. Recombinant protein was solubilized in 6 M urea and purified by nickel affinity and ion exchange chromatography. (This recombinant protein is hereinafter is referred to as "rDIV6728".)

After rDIV6728 was introduced into rabbits, anti-DIV6728 pAB was purified from the plasma of the immunized rabbits by isolating IgG antibody by protein G affinity chromatography. The protein-G purified polyclonal antibody anti-DIV6728 pAB was used in all Examples described herein, except for Example 3 (FIGS. 10A and 10B), where the anti-DIV6728 pAB used was affinity purified with rDIV6728 protein.

Infection and anti-helminth treatment of canine and feline animals. Parasitic nematode infection was effected by orally administering about 150-300 larvated eggs of either roundworm (*Toxocara*), hookworm (*Ancylostoma canium*), or whipworm (*Trichuris vulpis*) to a healthy canine or feline. (Specifically, *T. canis* was the roundworm that was administered to canine and *T. cati* was the roundworm that was administered to feline.) For Examples 1 and 2, fecal samples were collected from canines known to be naturally infected with heartworm (*Dirofilaria immitis*). Further, for Examples 4 and 6 only, canines were treated at post-infection day 91 with Interceptor® (milbemycin oxime), which is an anthelmintic agent commercially available from Novartis Animal Health Inc. of Basel, Switzerland, or felines were treated at post-infection day 56 with Drontal® (praziquantel/pyrantel pamoate), which is an anthelmintic agent commercially available from Bayer HealthCare, LLC of Shawnee Mission, Kans., according to the manufacturer's protocol. It is well known by those of ordinary skill in the art that Interceptor® and Drontal® are effective for the removal of roundworms (and other parasitic worms) from canines and felines, respectively, within 72 hours after treatment. Infection was confirmed by microscopic observation of worm ova in fecal samples obtained from these host animals.

Canine and feline fecal sample preparation. Canine and feline animals known to be free of parasitic worm infection or to be infected with one of either roundworm, hookworm, whipworm or heartworm provided the source of fecal samples. Samples (approximately 1 gram) from frozen, unpreserved canine or feline fecal samples were suspended in 4 ml of diluent solution ("diluent solution" is 0.05 M Tris base; 1 mM EDTA; 0.45% Kathon; 16 mg/ml gentamicin sulfate; 0.05% Tween-20; 40% fetal bovine serum; 10% rabbit serum; and 5% mouse serum). The suspension was centrifuged at 4000 rpm for 20 minutes to produce a first supernatant. The first supernatant was centrifuged at 12000 rpm for 5 minutes to produce a second supernatant, which is referred to herein as "fecal extract".

ELISA assays. Purified anti-DIV6728 pAB (100 μl/well; 3 μg/ml for Examples 2, 4 and 6; 10 μg/ml for Examples 1 and 5) was immobilized by physical adsorption on Immulon 1B 96-well plates overnight at 4° C. The plates were then blocked with 1% BSA in 0.1M Tris pH 7.0 at 4° C. overnight, followed by drying at room temperature. Approximately 100 μl of fecal extract was added to each well and allowed to incubate at room temperature for one hour. The wells were then washed five times with a PBS-Tween-20 solution according to standard methods known to those of ordinary skill in the art. In a separate reaction vessel, free anti-DIV6728 pAB was labeled with horseradish peroxidase (HRP) by using the crosslinker succinimidyl 4-[N-maleimidomethyl]cyclohexane-1-carboxylate (SMCC) to create a conjugate, and this conjugate (3 μg/ml for Examples 2, 4 and 6; 7.5 μg/ml for Examples 1 and 5) was added to each well having immobilized anti-DIV6728 pAB. Following a 30-minute incubation period at room temperature, unbound conjugate was washed from the wells by using PBS-Tween-20 solution according to standard methods known to those of ordinary skill in the art. 50 μl of TMBLUE® peroxidase substrate (SeraCare Life Sciences, West Bridgewater, Mass.) was then added to each well and the plates were incubated for 10 minutes at room temperature. After stopping each enzymatic reaction with 0.1% sodium dodecyl sulfate (SDS) following the 10-minute incubation period, the optical density (OD) value of each well of the 96-well plate was measured at A650 by standard spectrophotometric techniques by using an ELISA plate reader to generate an "OD650 value" (or, more simply, an "OD value") for each well. In this arrangement, the OD value obtained for any particular well of the 96-well plate was directly proportional to the amount of specifically bound antigen present in the well.

Example 1

Anti-DIV6728 pAB specifically binds roundworm coproantigen, but does not specifically bind coproantigen from either hookworm, whipworm or heartworm.

Figure 7:
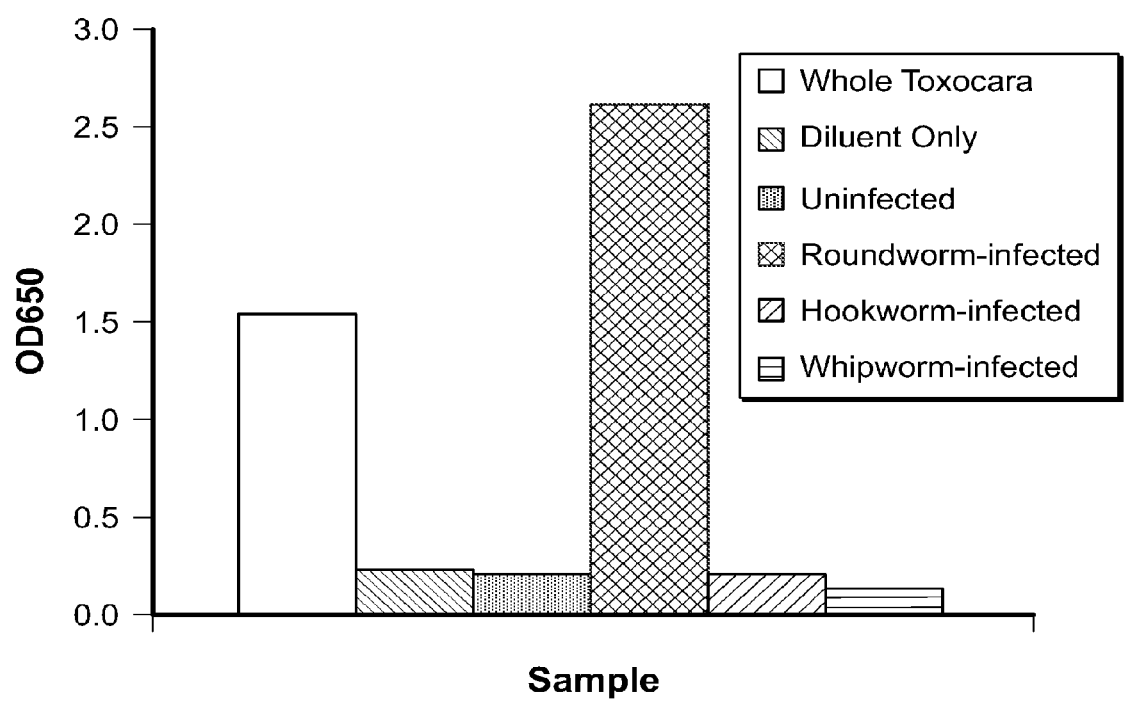
FIG. 7 shows a first graph of optical density (OD) values obtained from fecal samples from roundworm, hookworm, or whipworm-infected canines by following the method of the present invention in a first Example.

It was a goal of Example 1 to determine whether anti-DIV6728 pAB specifically binds coproantigen of roundworm in canines Measured OD values for pooled canine fecal extracts are shown in FIG. 7. Specifically, these fecal extracts were derived from fecal samples obtained from five canine animals known to be infected with roundworm ("Roundworm-infected"), two canine animals known to be infected with hookworm ("Hookworm-infected"), and five canine animals known to be infected with whipworm ("Whipworm-infected"). Additionally, OD values were also measured for whole Toxocara canis extract ("Whole Toxocara"; 1 μg/ml), which served as positive control, and for a pooled sample of fecal extracts obtained from five canines known to be free of parasitic worm infection ("Uninfected") and for a sample that did not contain any fecal extract ("Diluent Only"). (These latter two samples served as negative controls.)

Referring to FIG. 7, the OD value measured for the negative control diluent only sample was 0.23 and the negative control uninfected sample was 0.21.

Conversely, the measured OD value of the pooled fecal extract from the roundworm-infected canines was 2.62, which was more than 11 times higher than the OD values that were obtained for the negative control samples. These data indicate that anti-DIV6728 pAB specifically binds one or more roundworm coproantigens.

It was a second goal of Example 1 to determine whether anti-DIV6728 pAB specifically binds coproantigen of hookworm and/or whipworm. Referring to FIG. 7, the OD values measured for the hookworm-infected and whipworm-infected samples were 0.21 and 0.14, respectively which approximated or were lower than the measured OD values of the negative control diluent only sample (0.23) and the negative control uninfected sample (0.21), and were about 12 and about 18 times lower (respectively) than was the measured OD value of the roundworm sample (2.62). These data indicate that anti-DIV6728 pAB did not specifically bind coproantigen in either one of the samples obtained from the hookworm-infected and whipworm-infected canines.

Figure 8:
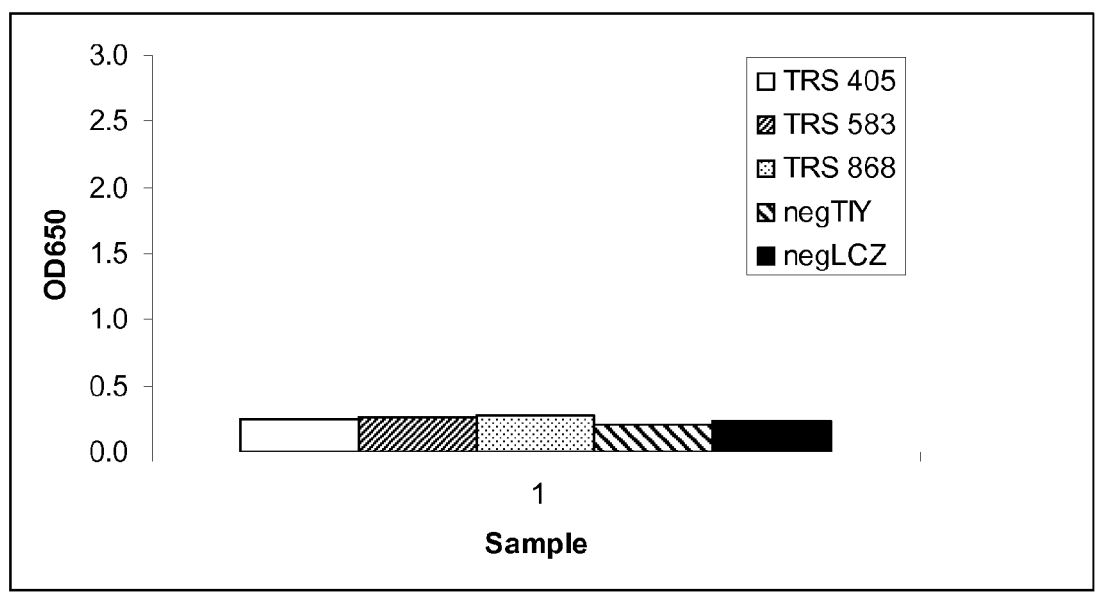
FIG. 8 shows a second graph of OD values obtained from fecal samples from canines infected with heartworm by following the method of the present invention in the first Example.

It was a third goal of Example 1 to determine whether anti-DIV6728 pAB specifically binds coproantigen of heartworm in canines Measured OD values for individual canine fecal extracts are shown in FIG. 8. Specifically, these samples were obtained from heartworm-infected canines that are identified as "TRS 405", "TRS 583", and "TRS 868" in FIG. 8. Further, an OD value also was measured for each one of two fecal extracts obtained from two canines that did not have a parasitic worm infection ("negTIY" and "negLCZ"). (These latter two extracts served as negative controls.)

Referring to FIG. 8, the OD values measured for the heartworm-infected samples was 0.25 for the TRS 405 canine and was 0.27 for each one of the TRS 583 and TRS 868 canines. These values approximated the OD values measured for the negative control samples (0.21 and 0.23), and were about 10 times lower than the measured OD value of the roundworm sample (2.62). These data indicate that anti-DIV6728 pAB did not specifically bind any coproantigen in the samples obtained from the heartworm-infected canines.

Example 2

When tested by ELISA in a microtiter dish format, anti-DIV6728 pAB specifically binds roundworm coproantigen, but does not specifically bind coproantigen from either hookworm, whipworm or heartworm, and specific binding of roundworm coproantigen by anti-DIV6728 pAB produces a colorimetric change that is readily observable to the human eye.

It was a goal of Example 2 to determine whether specific binding between anti-DIV6728 pAB and roundworm coproantigen while the anti-DIV6728 pAB is immobilized on a solid support can produce a colorimetric change that is observable to the human eye.

Figure 9:
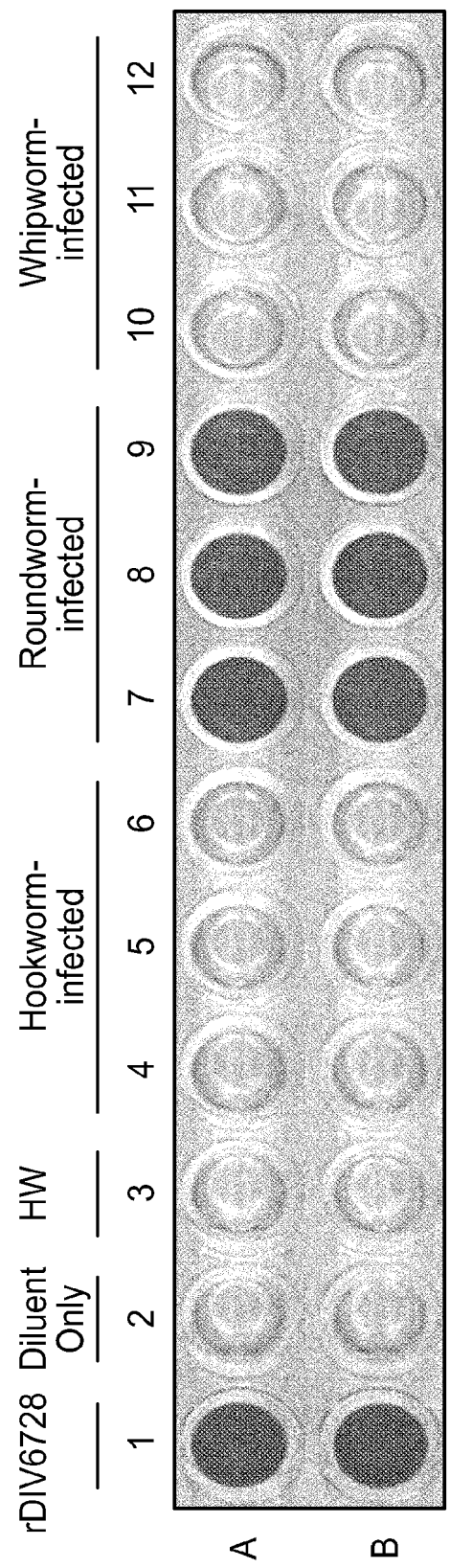
FIG. 9 shows the results of a first ELISA assay, which was carried out by using a microtiter plate and which tested fecal samples from canines infected with either roundworm, hookworm, whipworm or heartworm by following the method of the present invention in a second Example.

Referring to FIG. 9, anti-DIV6728 pAB (3 µg/ml) was immobilized onto the bottom surfaces of wells A1-A12 and B1-B12 of a microtiter plate as described before. Following such immobilization, the A3 and B3 wells were exposed to fecal extract from a heartworm-infected canine (indicated by "HW" in FIG. 9). The A4 and B4 wells were exposed to fecal extract from a first hookworm-infected canine, the A5 and B5 wells were exposed to fecal extract from a second hookworm-infected canine, and the A6 and B6 wells were exposed to fecal extract from a third hookworm-infected canine. The A7 and B7 wells were exposed to fecal extract from a first roundworm-infected canine, the A8 and B8 wells were exposed to fecal extract from a second roundworm-infected canine, and the A9 and B9 wells were exposed to fecal extract from a third roundworm-infected canine. The A10 and B10 wells were exposed to fecal extract from a first whipworm-infected canine, the A11 and B11 wells were exposed to fecal extract from a second whipworm-infected canine, and the A12 and B12 wells were exposed to fecal extract from a third whipworm-infected canine. The A1 and B1 wells were exposed to rDIV6728 (1 µg/ml), and therefore those wells served as positive controls. The A2 and B2 wells were not exposed to any fecal extract or to rDIV6728, and therefore those wells served as negative controls. After washing, all wells were exposed to HRP-labeled rDIV6728 pAB at 3 µg/ml as described above.

Following incubation of all of these wells with TMBLUE® peroxidase substrate and the subsequent addition of the SDS, colorimetric change was visually observed in each one the wells that had been exposed to fecal extract from roundworm-infected canines (A7-A9 and B7-B9), but no colorimetric change was observed in any of the wells that had been exposed to fecal extract from canines infected with either hookworm, whipworm or heartworm.

These data indicate that anti-DIV6728 pAB detects roundworm in an ELISA format sufficiently enough to produce a colorimetric change that is robust and readily visible to the human eye. Further, these data indicate that such colorimetric change allows the human eye to readily distinguish roundworm-positive fecal samples from those that do not contain roundworm, including those that include one or more of hookworm, whipworm, or heartworm.

Example 3

When tested by ELISA in a lateral flow format, anti-DIV6728 pAB specifically binds roundworm coproantigen and this specific binding of roundworm coproantigen by anti-DIV6728 pAB produces a colorimetric change that is readily observable to the human eye.

It was a goal of Example 3 to determine whether anti-DIV6728 pAB can be used to capture and detect roundworm coproantigen in a lateral flow ELISA. The lateral flow format that was used was a SNAP® assay device, similar to that which is described in U.S. Pat. No. 5,726,010. Further, the assay was performed generally as described in that same patent. Briefly, among other components, the SNAP® assay device included a sample entry cup, a flow matrix, a sample prefilter pad for removing interfering particulate matter, a specific binding reagent pad, a reactive zone, and an absorbent reservoir. Anti-DIV6728 pAB was immobilized in the form of a small, round spot at the reactive zone by drying (this bound anti-DIV6728 pAB is referred to hereinafter, in this Example only, as the "capture reagent".) The reactive zone was then blocked with BSA. A pooled fecal extract (150 µl) from roundworm-infected canines was mixed with 200 µl (1.0 µg/ml) conjugated anti-DIV6728 pAB (the anti-DIV6728 pAB was affinity-purified before being labeled with HRP as described above; this conjugated anti-DIV6728 pAB is referred to hereinafter, in this Example only, as the "detection reagent"). This mixture added to the sample cup and then was allowed to flow along the flow matrix. While in the flow matrix, the detection reagent specifically bound to roundworm coproantigens present in the fecal extract. The resulting complexes (i.e., those that included the detection reagent and the roundworm coproantigen) were allowed to specifically bind to the immobilized capture reagent at the reaction zone. Flow along the flow matrix was reversed by contacting the absorbent reservoir with the flow matrix. At this time, detector and wash solution migrated into the flow matrix to remove any unbound components and to allow detection of any analyte complexes that were present where the capture reagent was immobilized onto the reaction zone. (This detection step lasted about eight minutes.) Stopping of the detection of the analyte complexes occurred by exposing the analyte complexes to 0.1% azide.

Figure 10A:
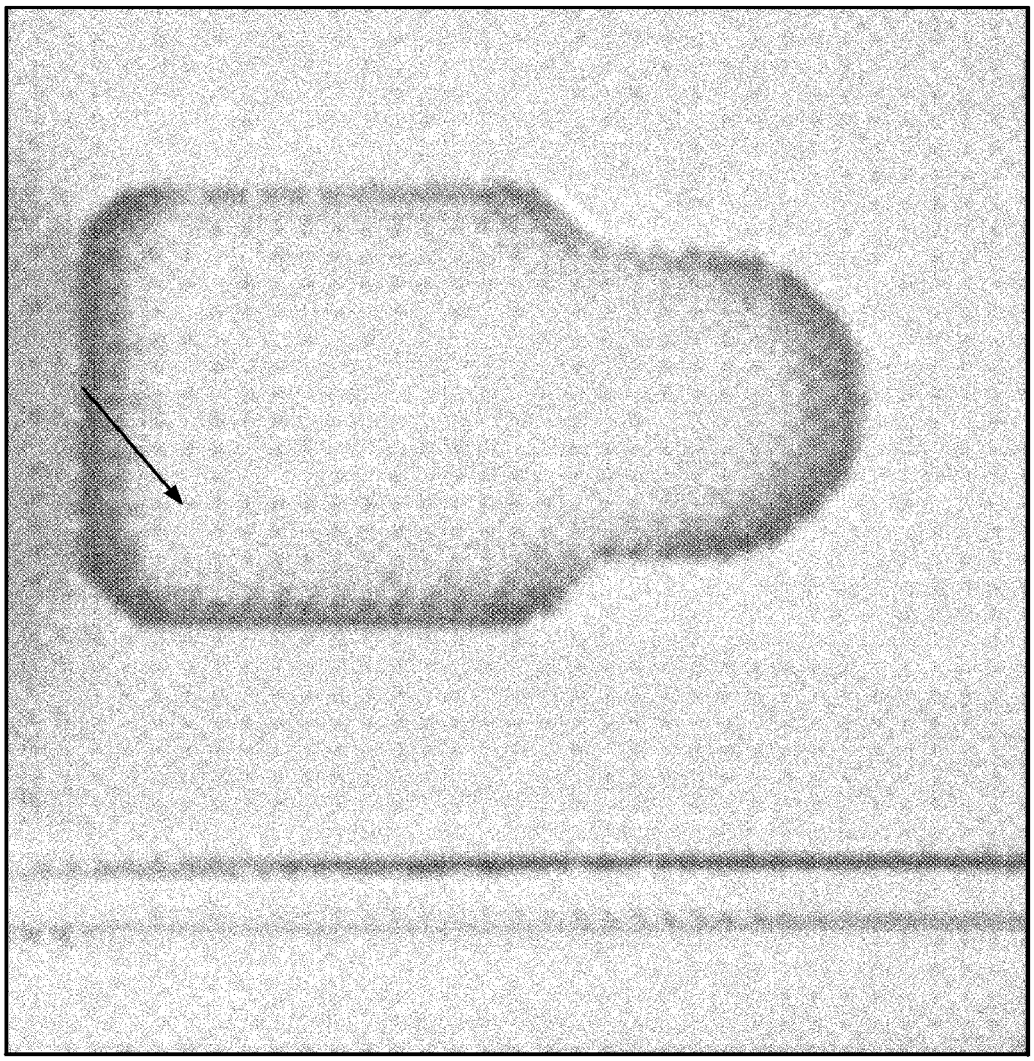
FIG. 10A shows the results of a second ELISA assay, which was carried out by using a lateral flow device and which tested fecal samples from canines infected with roundworm by following the method of the present invention in a third Example.
Figure 10B:
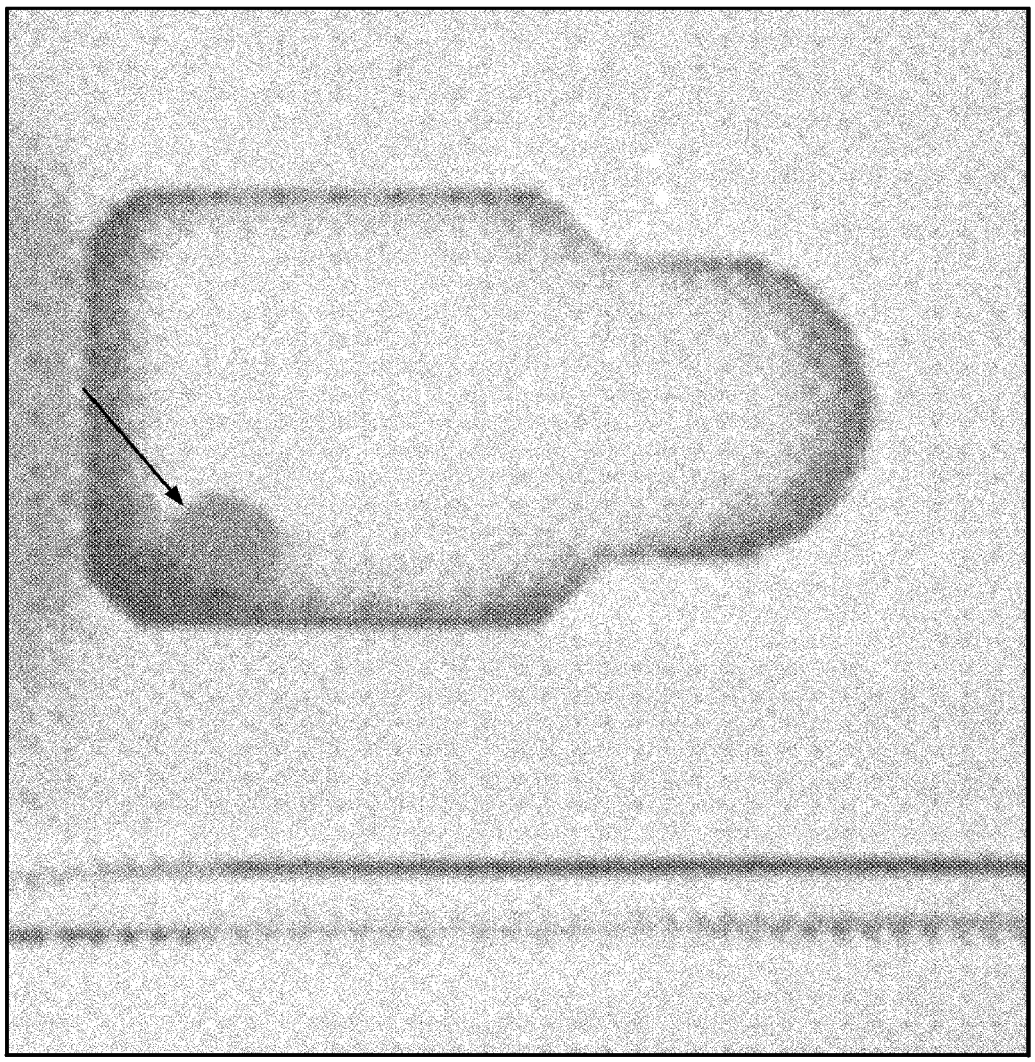
FIG. 10B shows the results of a third ELISA assay, which was carried out by using a lateral flow device and which tested fecal samples from canines that were not infected with roundworm by following the method of the present invention in the third Example.

As shown in FIG. 10A, detection of analyte complexes where the capture reagent was immobilized onto the reaction zone was visibly apparent (see the darkened spot indicated by the arrow). In a negative control sample shown in FIG. 10B, no analyte complexes were detected where the capture reagent was immobilized onto the reaction zone of a separate device. (The negative control assay was performed exactly as was the roundworm detection assay, with one exception, which was that the fecal extract that was used in the negative control was obtained from a canine that did not harbor a roundworm infection.) These data therefore indicate that anti-DIV6728 pAB can be used in a lateral flow ELISA format to specifically bind roundworm coproantigen. This specific binding is readily visible to the human eye.

Example 4

Anti-DIV6728 pAB does not detect roundworm in feces of canine animals that have had a roundworm infection, but that have been rid of that infection by the time the feces were excreted by the canines.

Figure 11:
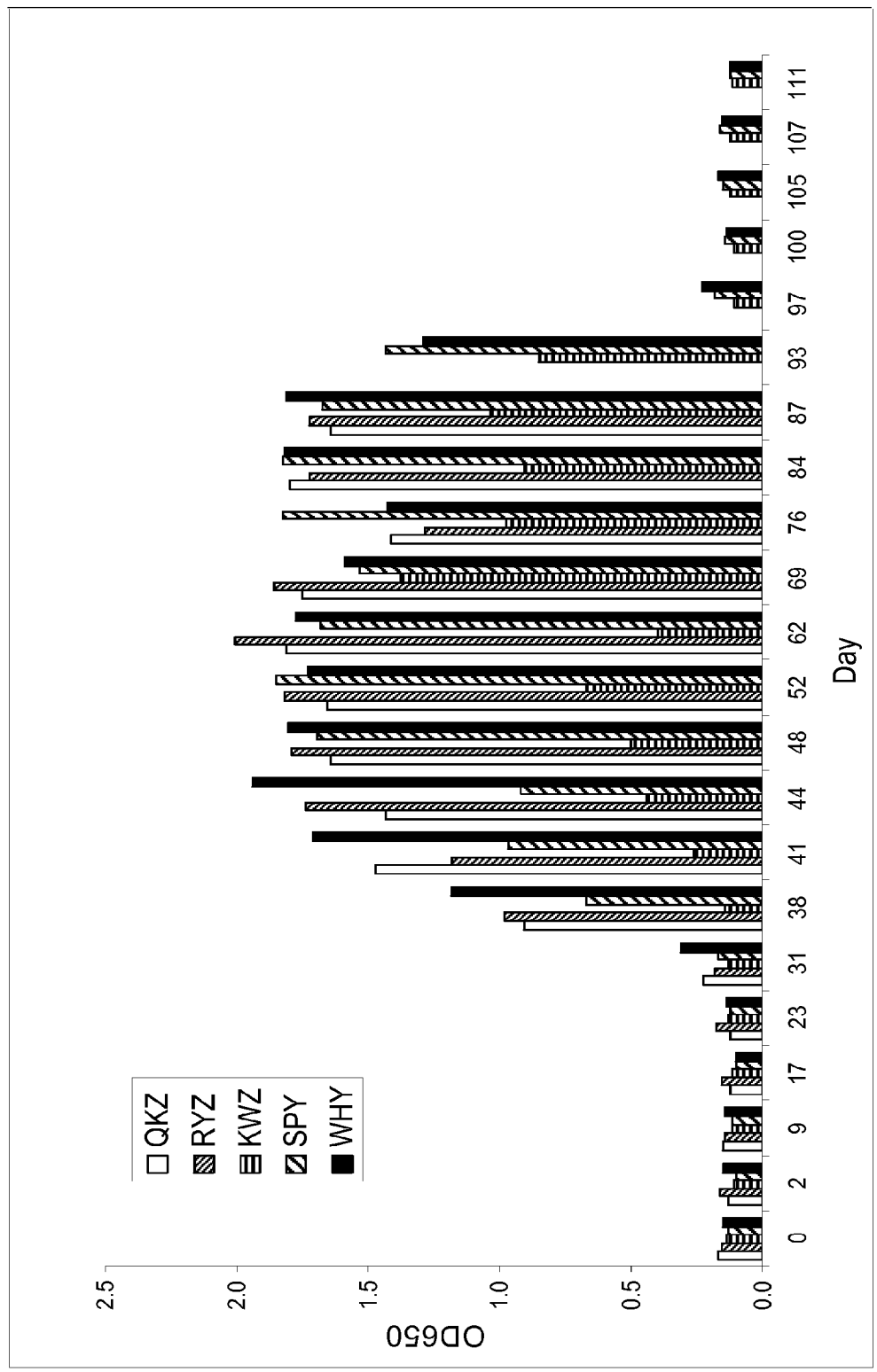
FIG. 11 shows a first graph of OD values obtained from fecal samples from a set of canines that had an active roundworm infection and from fecal samples from those canines after they had been rid of their active roundworm infection by following the method of the present invention in a fourth Example.
Figure 12:
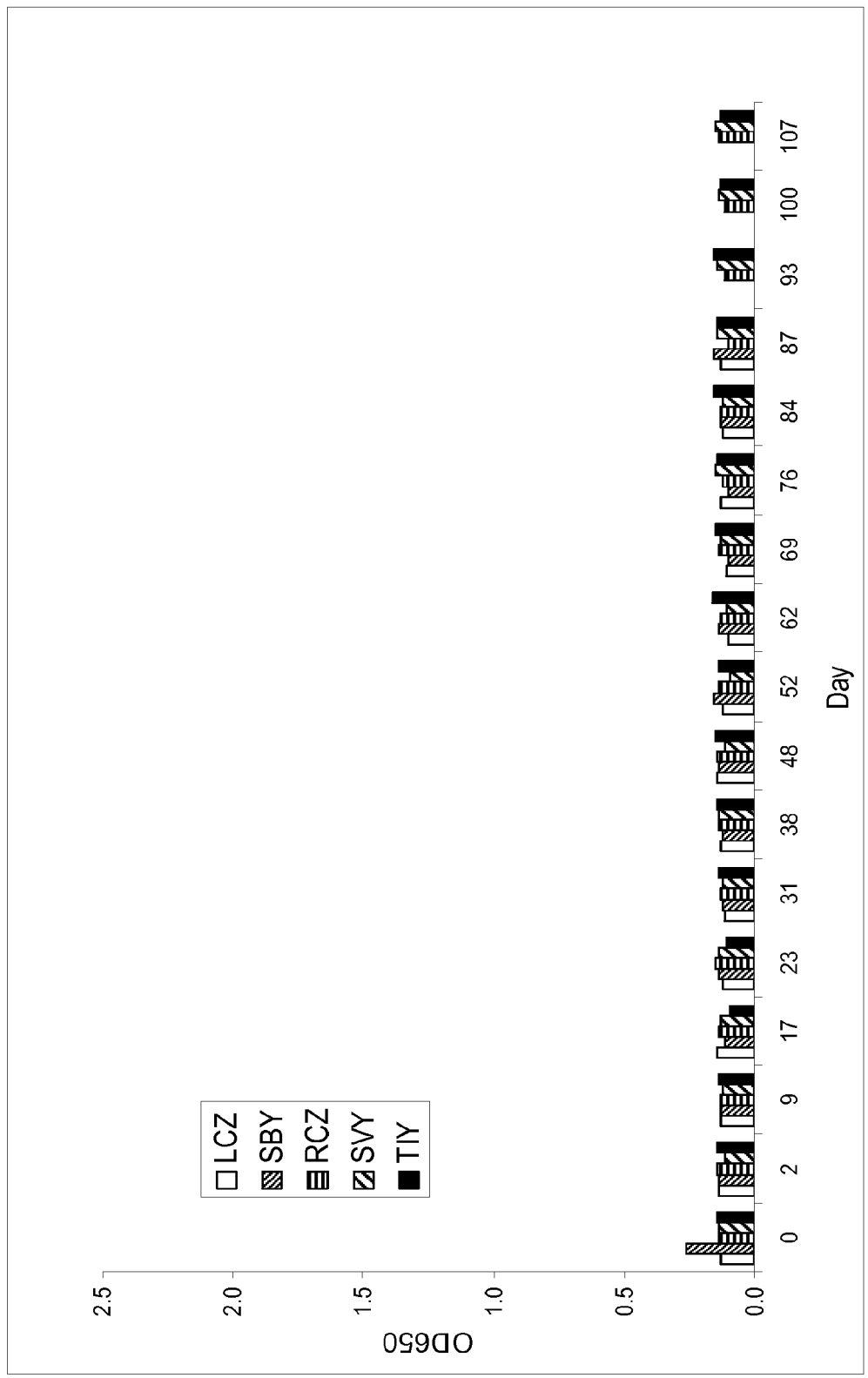
FIG. 12 shows a second graph of OD values obtained from fecal samples from a set of felines that did not have a parasitic worm infection by following the method of the present invention in the fourth Example.

It was a goal of Example 4 to determine whether anti-DIV6728 pAB detects roundworm in feces of canine animals that have been rid of a prior roundworm infection. OD values measured for fecal samples obtained from a first set of five canines and a second set of five canines are shown in FIGS. 11 and 12, respectively. The first set of canines, which are identified as "QKZ", "RYZ", KWZ", "SPY" and "WHY", were infected with roundworm on day 0 and were treated with the Interceptor® anthelmintic agent on day 91 after the administration of the infection as described before. Fecal samples were taken from all or some of the first set of canines on day 0, on day 2 and day 111 following the administration of the roundworm infections to these animals, and on selected days between day 2 and day 111. Microscopic observation of the fecal samples from the first set of canines confirmed that each one of the samples taken at day 0 through day 31 and at day 100 through day 111 was substantially free of roundworm ova, and that, with one exception, such ova were present only in the samples at each one of days 38 through 97. (The lone exception being that ova were not observed in the day 38 fecal sample from the KWZ canine.)

The second set of canines, which are referred to as "LCZ", "SBY", RCZ", "SVY" and "TIY", were never infected with roundworm (and therefore this second set of canines served as negative controls). Fecal samples were taken from each one of these canines on the day that the first set of canines were infected with roundworm (day 0). Further, fecal sample were taken from these second set of canines on day 2 and day 107 following the administration of the roundworm infections to the first set of canines, and on selected days between day 2 and day 107. Microscopic observation of the fecal samples from the second set of canines confirmed that each one of the samples taken at day 0 through day 107 was free of roundworm ova.

Referring to FIG. 11, the OD values measured for the fecal samples taken from the first set of canines (i.e., the canines that were infected with roundworm) at days 38 through 93 were many times higher than were the OD values measured for fecal samples from those same canines following their treatment with the anthelmintic agent. Further, the OD values measured for the fecal samples taken from the first set of canines at days 38 through 93 were many times higher than for each one of the negative control samples of FIG. 12. These data further indicate that anti-DIV6728 pAB does not detect roundworm in feces from a canine that has been rid of a prior roundworm infection.

Example 5

Anti-DIV6728 pAB specifically binds roundworm antigen in fecal samples obtained from roundworm-infected feline animals.

Figure 13:
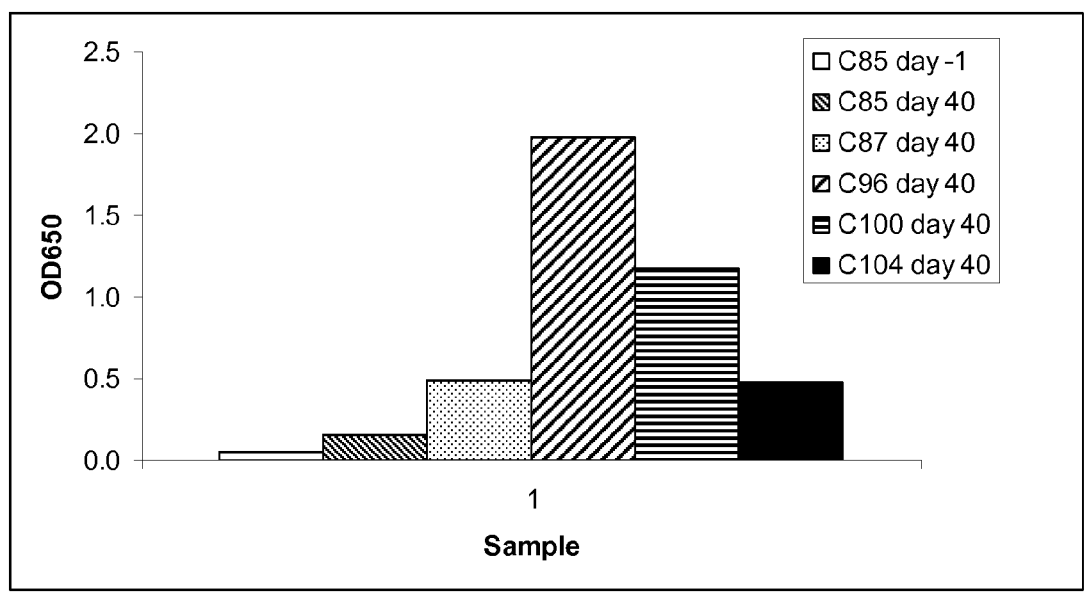
FIG. 13 shows a graph of OD values obtained from fecal samples from roundworm-infected felines by following the method of the present invention in a fifth Example.

It was a goal of Example 5 to determine whether anti-DIV6728 pAB specifically binds roundworm coproantigen in felines. OD values measured for fecal samples obtained from uninfected felines and roundworm-infected felines are shown in FIG. 13. Specifically, these OD values were measured from fecal samples taken from five different roundworm-infected felines (represented by the identifiers "C85", "C87", "C96", "C100" and "C104") 40 days following administration of a roundworm infection to those felines. As a negative control, OD values also were measured from a fecal sample obtained from the C85 feline one day prior to the administration of the roundworm infection to that feline ("day −1").

Referring to FIG. 13, the OD value measured for the uninfected feline (C85 at day −1) was 0.06. The OD values of the five felines at day 40 ranged from about three times (the OD value of the C85 feline at day 40 was 0.16) to more than 30 times (the OD value of the C96 feline was 1.98) greater than was the OD value measured for the uninfected feline. These data indicate that anti-DIV6728 pAB specifically binds one or more roundworm coproantigens in feline.

Example 6

Anti-DIV6728 pAB does not detect roundworm in feces of feline animals that have had a roundworm infection, but that have been rid of that infection by the time the feces were excreted by the felines.

Figure 14:
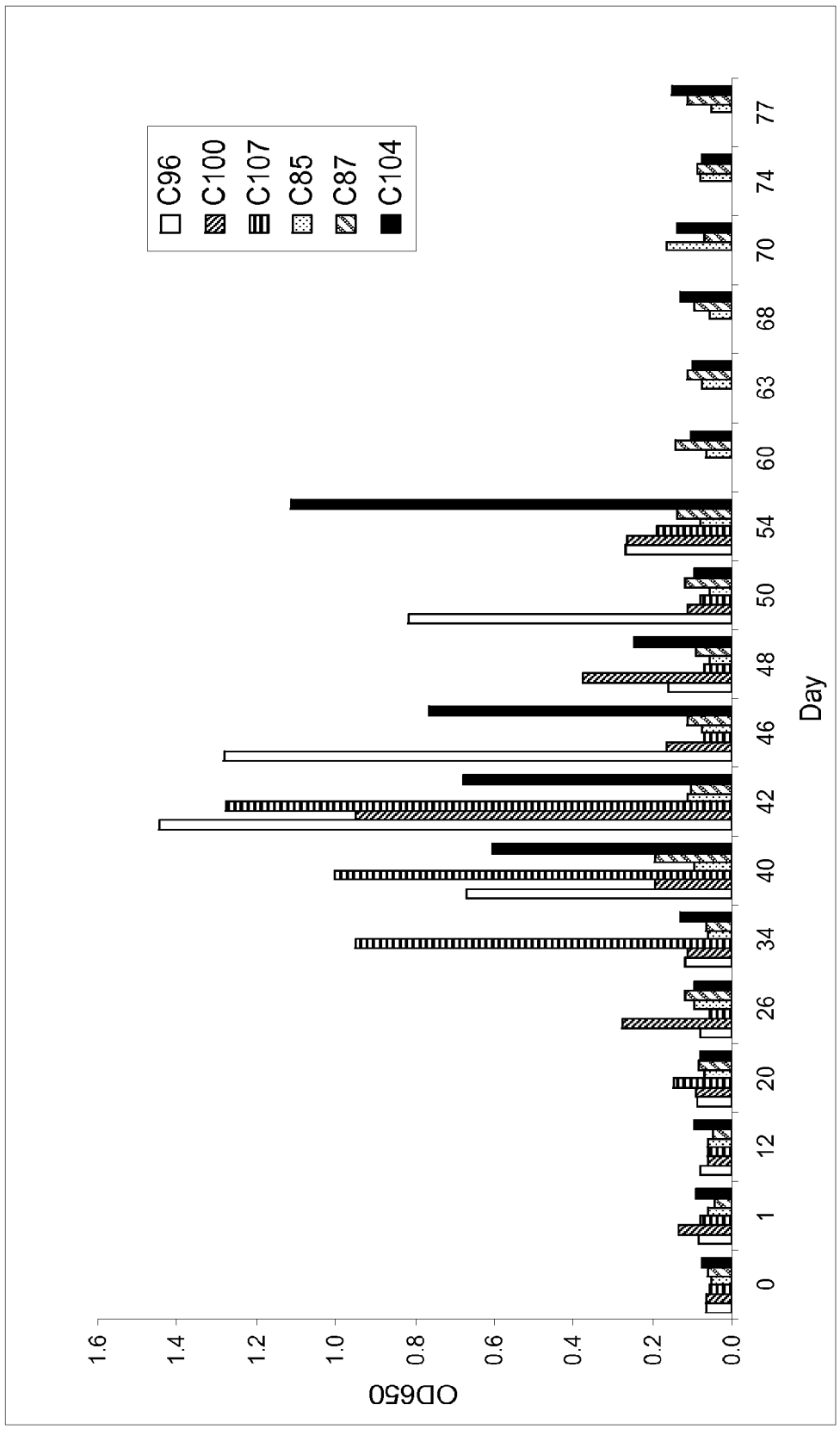
FIG. 14 shows a first graph of OD values obtained from fecal samples from a set of felines that had an active roundworm infection and from fecal samples from those felines after they had been rid of their active roundworm infection by following the method of the present invention in a sixth Example.
Figure 15:
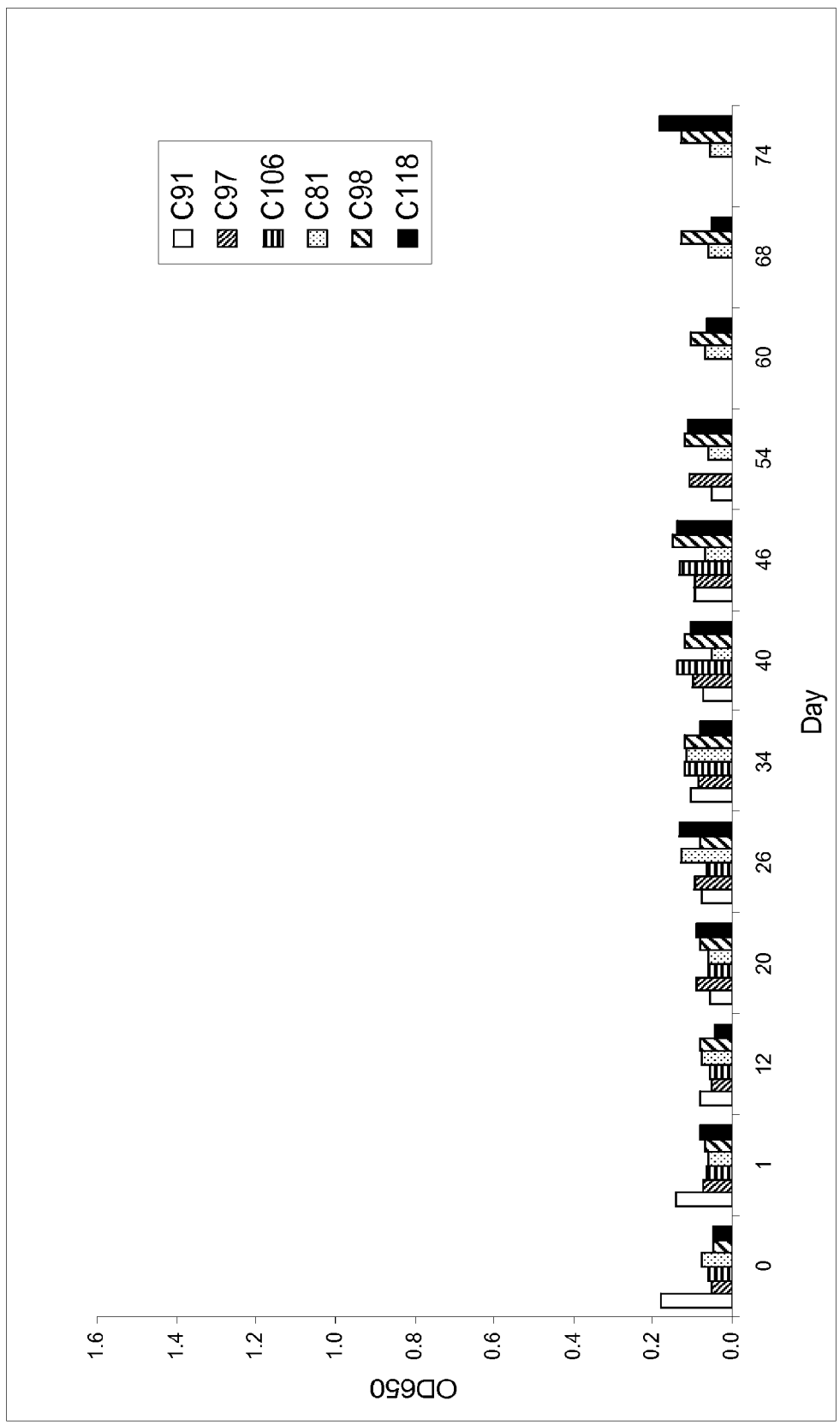
FIG. 15 shows a second graph of OD values obtained from fecal samples from a set of felines that did not have a parasitic worm infection by following the method of the present invention in the sixth Example.

It was a goal of Example 6 to determine whether anti-DIV6728 pAB detects roundworm in feces of feline animals that have been rid of a prior roundworm infection. OD values measured for fecal samples obtained from a first set of six felines and a second set of six felines are shown in FIGS. 14 and 15, respectively. The first set of felines, which are identified as "C96", "C100", C107", "C85", "C87" and "C104", were infected with roundworm on day 0 and were treated with the Drontal® anthelmintic agent on day 56 after the administration of the infection as described before. Fecal samples were taken from all or some of the first set of felines on day 0, day 1 and day 77 following the administration of the roundworm infections to these animals, and on selected days between day 1 and day 77. Microscopic observation of the fecal samples from the first set of felines confirmed that each one of the samples taken at day 0 through day 26 and at day 60 through day 77 was substantially free of roundworm ova, and that such ova were present in each one of the day 34 through day 54 samples.

The second set of felines, which are identified as "C91", "C97", C106", "C81", "C98" and "C118", were never infected with roundworm (and therefore served as negative controls). Fecal samples were taken from each one of these felines on the day that the first set of felines were infected with roundworm (day 0). Further, fecal sample were taken from these second set of felines on day 1 and day 74 following the administration of the roundworm infections to the first set of felines, and on selected days between day 1 and day 74. Microscopic observation of the fecal samples from the second set of felines confirmed that each one of the samples taken at day 0 through day 74 was free of roundworm ova.

Referring to FIG. 14, the OD values measured for several of the fecal samples taken from the first set of felines (i.e., the felines that were infected with roundworm) at days 34 through 54 were many times higher than were the OD values measured for fecal sample samples from those same felines following their treatment with the anthelmintic agent. Further, the OD values measured for several of the fecal samples taken from the first set of felines at days 34 through 54 were many times higher than for each one of the negative control samples of FIG. 15. These data indicate that anti-DIV6728 pAB does not detect roundworm in feces from a feline that has been rid of a prior roundworm infection.

Example 7

A truncated version of DIV6728, Copro6728, is present in *T. canis* infected canine feces A. Canine Fecal Sample Preparation Canine animals known to harbor a roundworm (*T. canis*) infection or to not have a parasitic worm infection provided the source of fecal samples. A sample (approximately 1 gram) of frozen, unpreserved canine feces pooled from five roundworm-infected or uninfected canines was suspended in 4 ml of extraction buffer ("extraction buffer" is 1× phosphate-buffered saline (PBS), pH 7.0-7.5 with 0.05% Tween-20). This suspension was vortexed for 2 minutes and then was centrifuged at 13,000 rpm for 25 minutes to produce a first supernatant. This first supernatant was then centrifuged at 10,000 rpm for 5 minutes to produce a second supernatant. This second supernatant hereinafter is referred to as "fecal extract".

B. Ion Exchange

Figure 16:
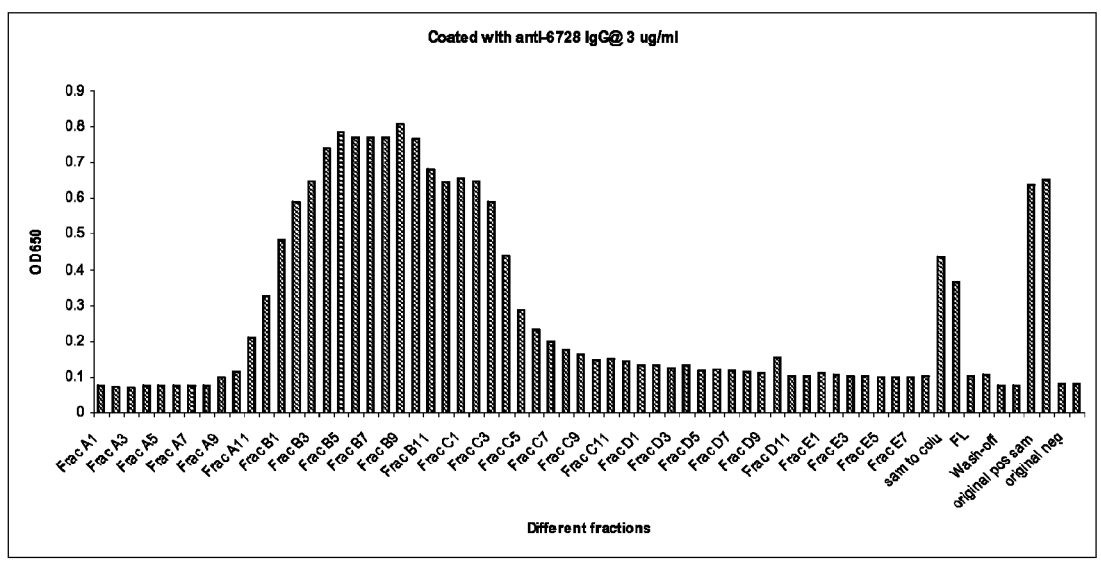
FIG. 16 shows an ELISA with elution fractions from a sulfopropyl (SP) columns as samples and that Copro6728 can be partially purified and enriched by eluting the SP column by following the method of the present invention in the seventh Example.

Ion exchange chromatography can enrich Copro6728 from a fecal sample. PLRS samples were used for this study. Fecal sample was extracted first with PBST (0.05% Tween 20), pH 7.3. Sample was diluted with sodium citrate buffer, pH 3.0 first and then the pH was adjusted to 3 with HCl. Finally, sample was centrifuged and the supernatant was loaded onto a sulfopropyl (SP) column (HiTrap SP Sepharose column, GE Healthcare). The SP column was eluted with 20 mM sodium citrate buffer, pH 3 with 1 M NaCl, and the elution fractions were evaluated by ELISA. The ELISA plate was coated with rabbit anti-6728 IgG at 3 µg/ml. Based on the results shown in FIG. 16, it is clear that Copro6728 can be partially purified and enriched by eluting the SP column with sodium citrate buffer with 1 M NaCl and Copro6728 is in the fraction between A11 and C9 (FIG. 16).

C. Western Blotting and SDS-PAGE

Figure 17:
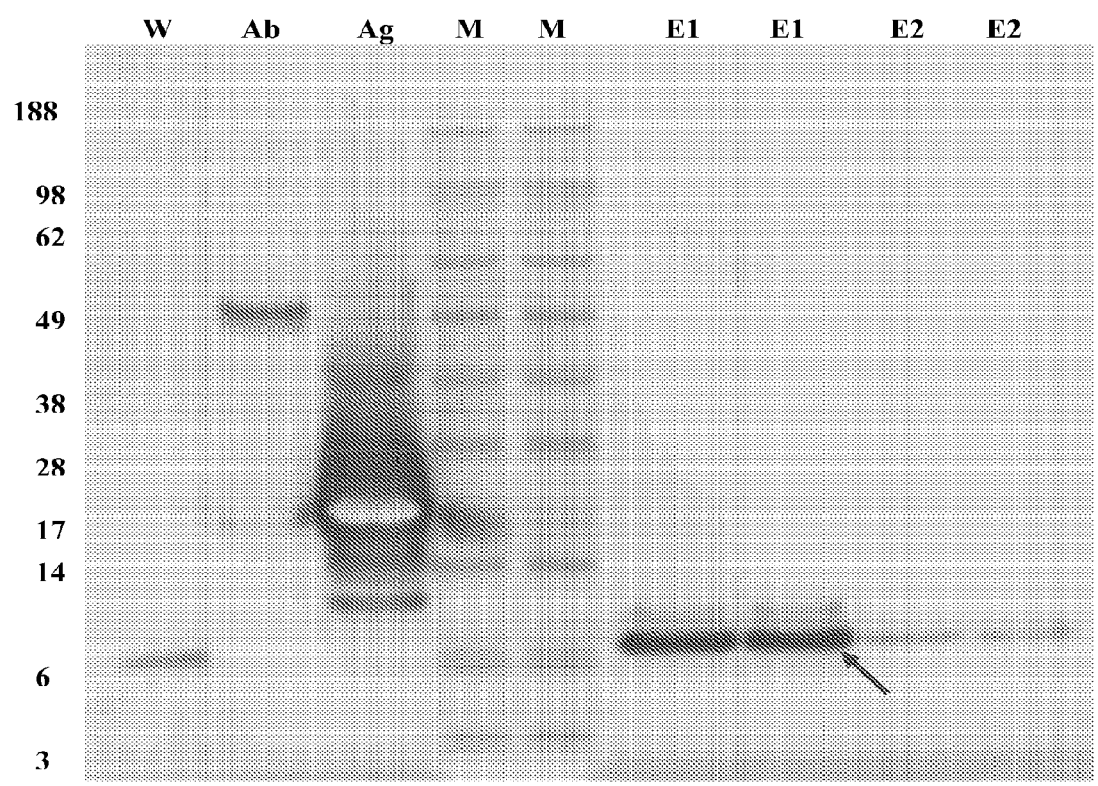
FIG. 17 shows that the molecular weight of Copro6728 was about 7 KD using a western Blot probed with rabbit anti full-length DIV6728 IgG-HRP following the method of the present invention in the seventh Example.
Figure 18:
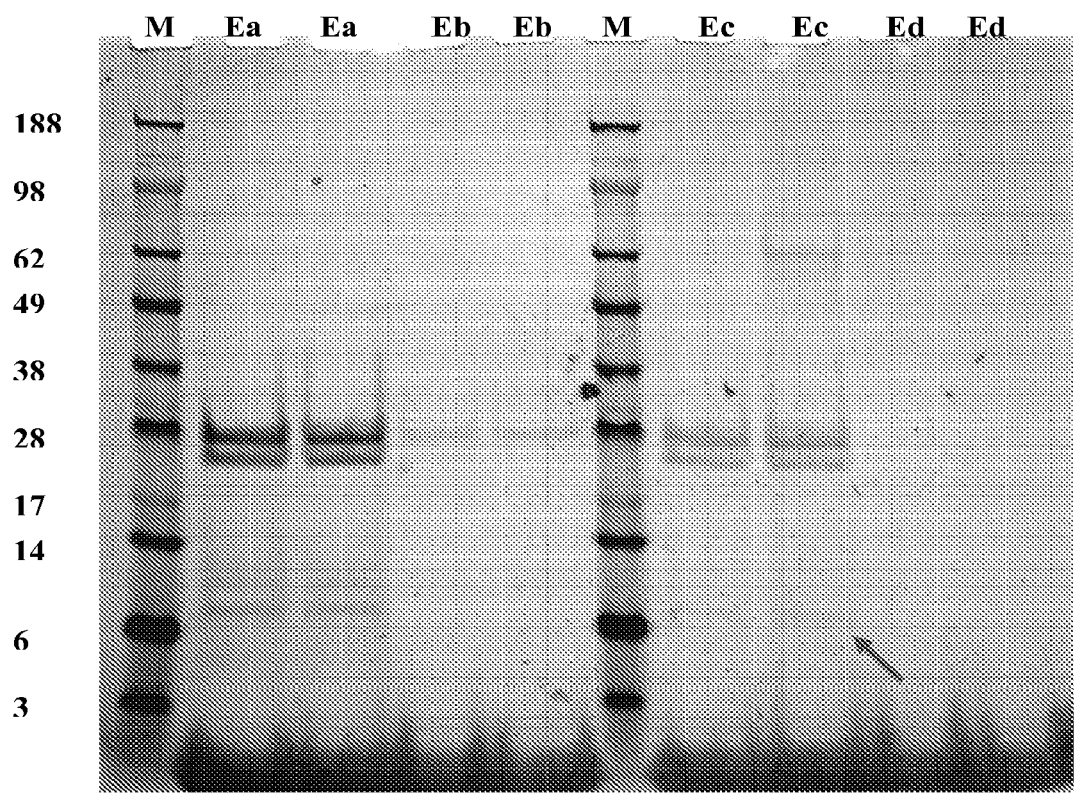
FIG. 18 shows that the molecular weight of Copro6728 was about 7 KD using an SDS-PAGE gel stained with Imperial Protein Staining following the method of the present invention in the seventh Example.

Western blotting and SDS-PAGE gel showed that the molecular weight of Copro6728 is about 7 kD. Elution fractions from the SP column were mixed and buffer pH was adjusted to 7 with NaOH before loading onto an affinity column, which was prepared by linking the rabbit anti-6728 IgG with AminoLink resin (Pierce, Thermo Scientific). The column was washed and eluted according to manufacturer's instructions. Elution fractions were loaded to a 10 well 4-12% Bis-Tris gradient gel and transferred to nitrocellulose membrane for western blotting. Probed with rabbit anti-6728IgG-HRP, western blotting showed that the major band (Copro6728) is about 7 kD (red arrow on FIG. 17). After further concentration, the same samples were visualized on an SDS-PAGE gel with Imperial Protein Stain (Pierce, Thermo Scientific). A 7 kD band corresponding to the size indicated by anti-6728IgG-HRP is visible (red arrow on FIG. 18).

D. Mass Spectrometry Analysis

Mass spectrometry analysis on the band cut from SDS-PAGE gel (pointed by a red arrow on FIG. 18) indicated that this band contains Copro6728, and that the C-terminal portion of DIV6728 contains Copro6728.

The 7 kD band that corresponds to the 7 kD band on the Western blotting was cut out from the SDS-PAGE gel and sent to the Keck Center at Yale University for Mass spectrometry analysis. The sample in the gel was first trypsin digested and then analyzed by LC-MS/MS using the Q-T of of Ultima Mass spectrometer (Waters). Two specific peptides were found in the sample by Mass Spectrometry analysis: Peptide 1: R.FVPCTR.N (SEQ IS NO: 8) and Peptide 2: R.DAEGN-CIK.F (SEQ ID NO: 9).

Alignment analysis on the sequences of DIV6728 (SEQ ID NO: 5) and the two peptides identified by MS analysis indicated that both peptides are located in the C terminal half of the full-length DIV6728, confirming that the 7 kb band identified by Western blot is derived from DIV6728. The location of the two peptide sequences indicates that a C-terminal portion of DIV6728 (Copro6728) was present in the *T. canis* positive fecal samples. FIG. 19 shows the full-length of DIV6728 (SEQ ID NO: 5) with the two peptides identified by MS analysis highlighted in the shaded boxes.

Example 8

Two recombinant proteins were generated that correspond to 64 amino acids within the N-terminal portion of DIV6728 and 65 amino acids within the C-terminal portion of DIV6728.

Based on the MS analysis, western blotting and SDS-PAGE data, two new expression constructs encoding truncations of DIV6728 were made. They were named 6728N (SEQ ID NO: 10) and 6728C (SEQ ID NO: 11) for the N-terminus and C-terminus of full-length DIV6728, respectively. FIG. 20 shows an alignment of the 6728N (SEQ ID NO: 10) and 6728C (SEQ ID NO: 11) amino acid sequences encoded by the constructs.

A. Synthetic Genes for Expressing Recombinant 6728N and 6728C

The genes for expressing 6728N and 6728C polypeptides were codon optimized for expression in *E. coli*, synthesized and cloned into vector pET28(a) with His(6) tags at the N-terminus of each recombinant protein by GeneArt (Josef-Engert-Str. 11D-93053 Regensburg, Germany).

B. Recombinant Protein 6728N and 6728C Expression

Figure 21:
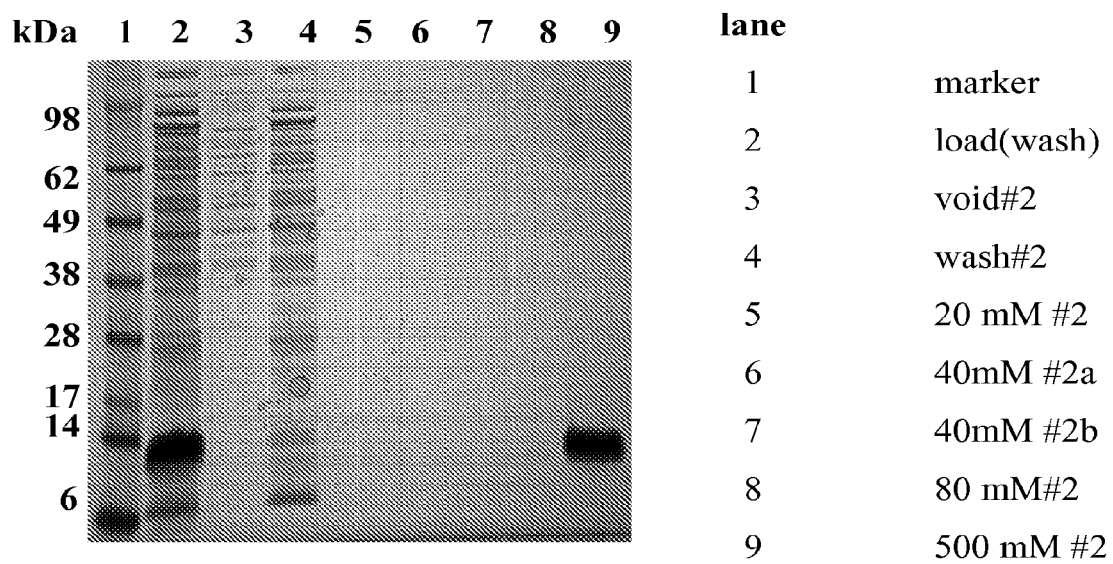
FIG. 21 shows a SDS-PAGE gel loaded with different samples to check the purification of the recombinant 6728N following the method of the present invention in the eighth Example.

Recombinant proteins 6728N and 6728C were expressed in *E. coli* BL21(DE3) and purified with a single nickel column. Plasmid pET28(a) 6728N was transformed into BL21 (DE3), grown to an OD~0.8 and induced with 1 mM IPTG (Isopropyl-1-thio-β-D-galactopyranoside) at 37° C. for 2 hour. Cells were lysed with Microfluidizer® Processor, M-11EH. Recombinant 6728N was soluble in the 20 mM Tris buffer, pH 8.0, with 500 mM NaCl and was purified by step eluting the nickel column with different concentration of imidazole in the 20 mM Tris buffer, pH 8.0, with 500 mM NaCl. The recombinant 6728N was eluted from the Nickel column by the same buffer with 500 mM imidazole. FIG. 21 is a SDS-PAGE gel loaded with different samples to check the purification of the recombinant 6728N. Recombinant 6728N is about ~12 kD in size (lane 9) on the gel.

Figure 22:
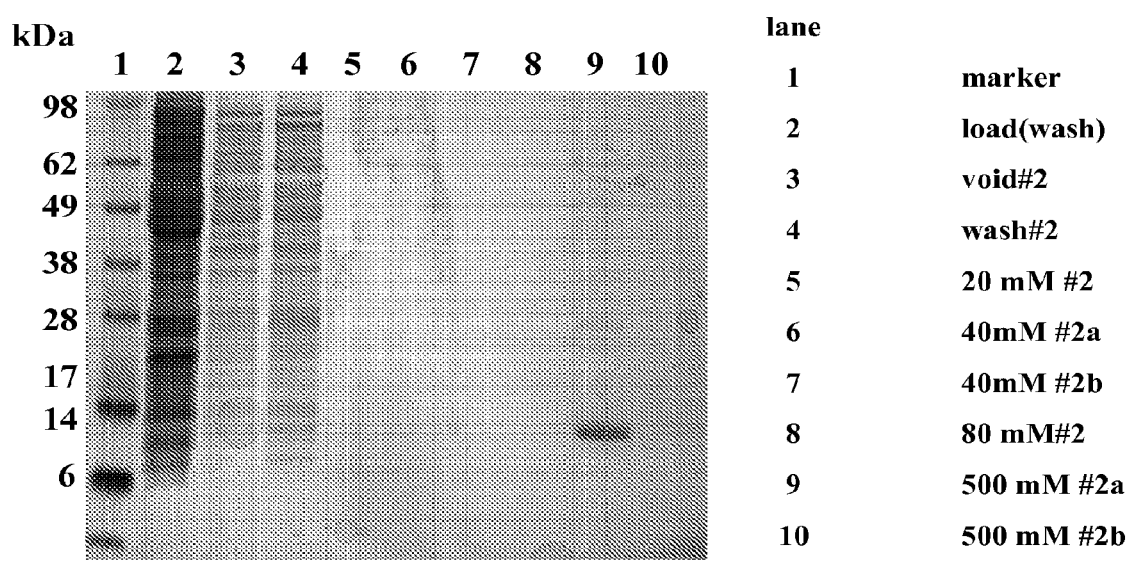
FIG. 22 shows a SDS-PAGE gel loaded with different samples to check the purification of the recombinant 6728C following the method of the present invention in the eighth Example.

Plasmid pET28(a) 6728C was transformed into BL21 (DE3), grown to an OD ~0.8 and induced with 1 mM IPTG (Isopropyl-1-thio-β-D-galactopyranoside) at 37° C. for 2 hour. Cells were lysed with Microfluidizer® Processor, M-11EH. Recombinant 6728C was soluble in the 20 mM Tris buffer, pH 8.0, with 500 mM NaCl and was purified by step eluting the nickel column with different concentration of imidazole in the 20 mM Tris buffer, pH 8.0, with 500 mM NaCl. The recombinant 6728C was eluted from the Nickel column by the same buffer with 500 mM imidazole. FIG. 22 is a SDS-PAGE gel loaded with different samples to confirm the purification of the recombinant 6728C. Recombinant 6728C is about ~12 kD in size (lane 9) on this gel.

C. Rabbit Polyclonal Antibodies

Figure 23:
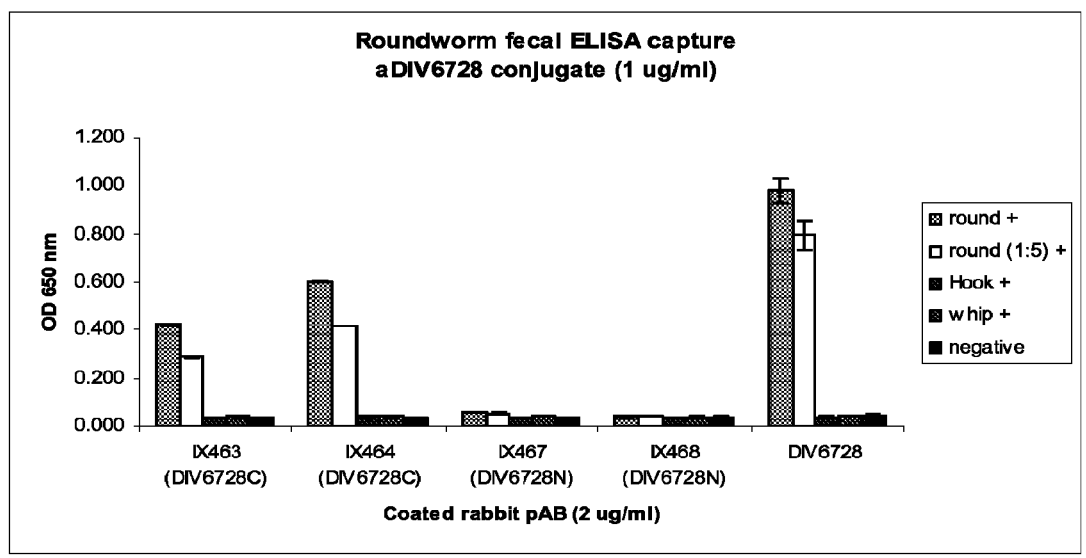
FIG. 23 shows the ELISA data obtained with different fecal samples to test the different polyclonal antibodies against different recombinant 6728 proteins following the method of the present invention in the eighth Example.
Figure 24:
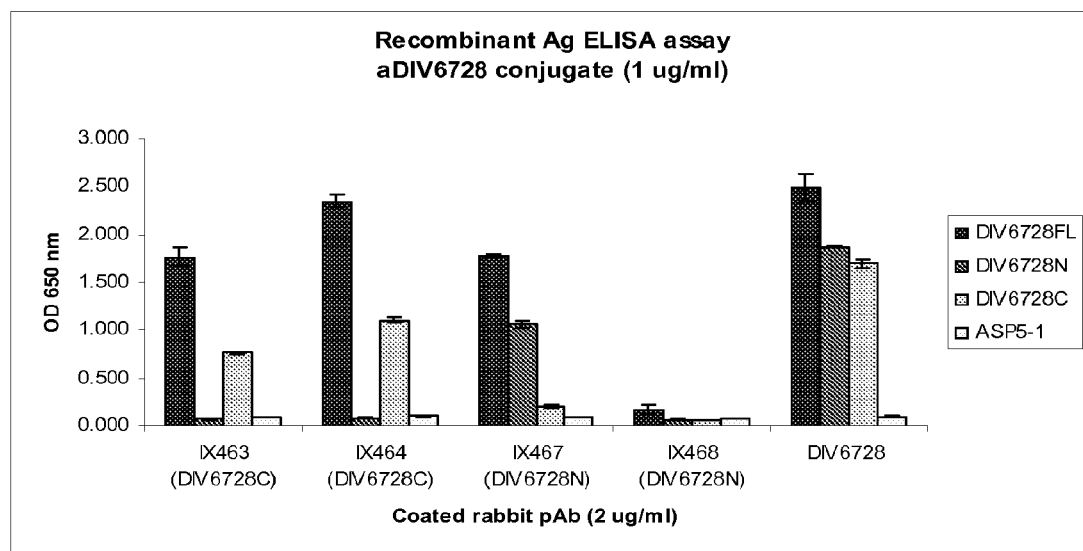
FIG. 24 shows the ELISA data obtained with recombinant proteins to test the different polyclonal antibodies against different recombinant 6728 proteins following the method of the present invention in the eighth Example.

Rabbit polyclonal antibody raised against 6728C detects antigen in fecal ELISA, whereas polyclonal antibody against 6728N does not detect antigen in fecal ELISA Recombinant proteins 6728N and 6728C, purified with a single Nickel column, were used to immunize rabbits for polyclonal antibody production. Polyclonal antibodies from the immunized rabbit sera were affinity purified with Protein G resin and used to coat Immulon I plates at 2 µg/ml. Four different canine samples were tested with different antibody coated plates. Antibodies from the two rabbits immunized with recombinant 6728C could differentiate the *T. canis* positive fecal samples from hookworm, whipworm positive samples and nematode negative samples. However, antibodies from the two rabbits immunized with recombinant 6728N could not differentiate the *T. canis* positive fecal samples from hookworm, whipworm positive samples and nematode negative samples (FIG. 23). This ELISA data further demonstrates that Copro6728 is a C-terminal portion of full-length DIV6728. Further experiments showed that antibodies raised against 6728N and 6728C only recognize their cognate recombinant proteins without cross reactivity. (FIG. 24). Both of these polyclonal antibodies react with full-length recombinant DIV6728 as expected (FIG. 24).

D. Western Blotting

Figure 25:
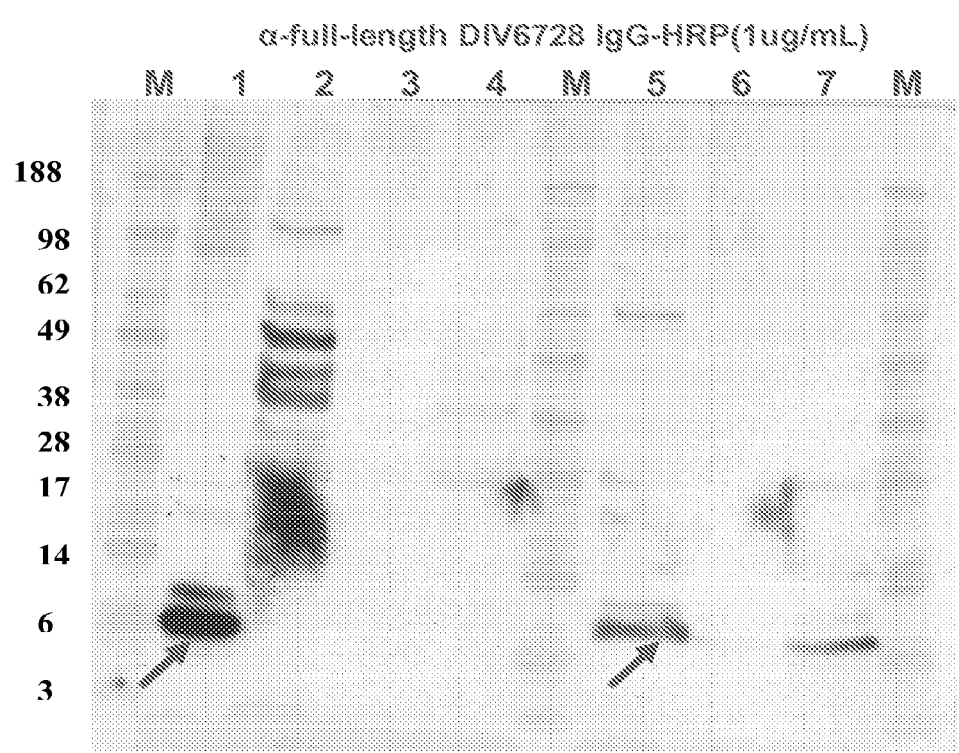
FIG. 25 shows Western blotting with different fecal samples probed with rabbit anti-full-length DIV6728 IgG-HRP following the method of the present invention in the eighth Example.
Figure 26:
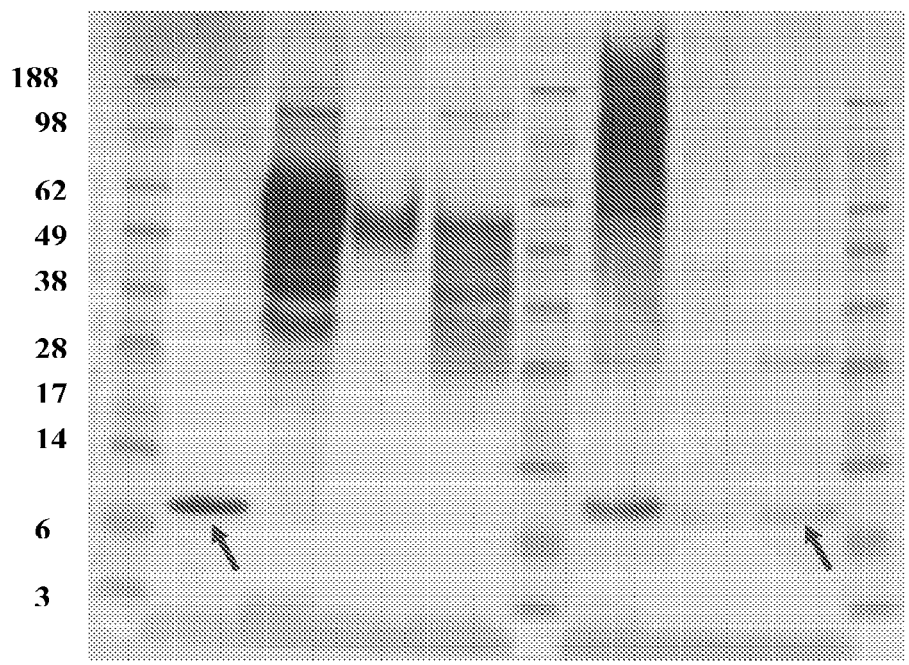
FIG. 26 shows Western blotting with different fecal samples probed with rabbit anti-6728C IgG-HRP following the method of the present invention in the eighth Example.
Figure 27:
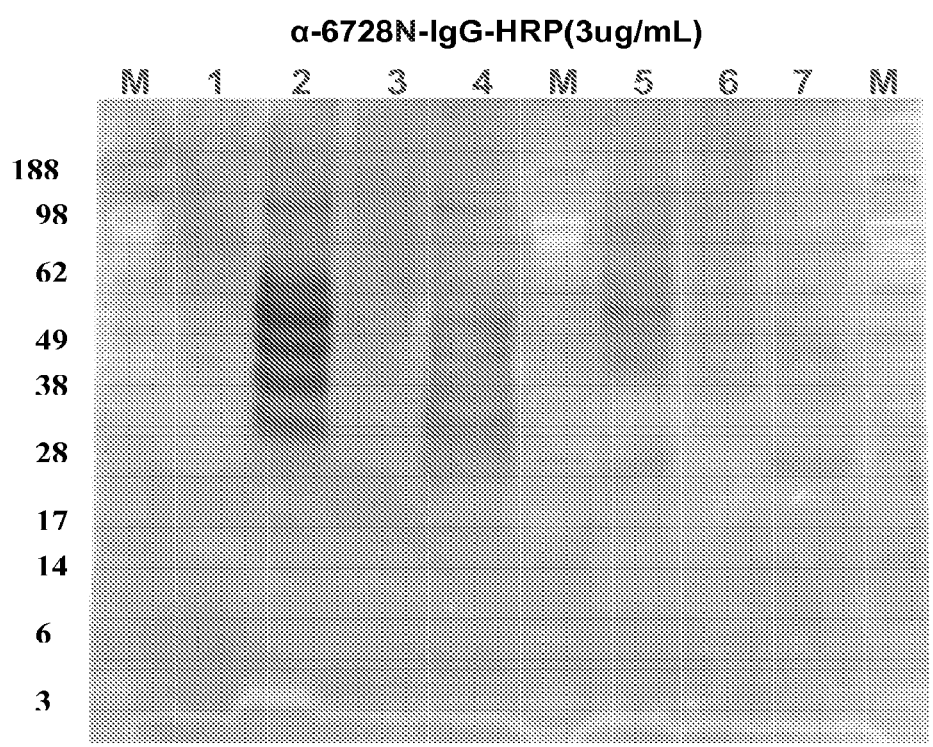
FIG. 27 shows Western blotting with different fecal samples probed with rabbit anti-6728N IgG-HRP following the method of the present invention in the eighth Example.

Rabbit polyclonal antibody against recombinant 6728C can recognize the *T. canis* positive fecal samples in Western Blotting, but not the polyclonal antibody against recombinant 6728N. In addition to *T. canis* whole worm extract (lane 1), nematode negative (lanes 2-4) and *T. canis* positive (lanes 5-7) fecal samples were fractionated by SP column with high salt elution buffer (1 M NaCl in 20 mM sodium citrate buffer, pH 3). The *T. canis* worm extract (lane 1), samples loaded onto the column (lane 2 and 5), column flow-through (lane 3 and 6), and column elution (lane 4 and 7) were loaded to 10 well, 4-12% Bis-Tris gradient gel and then further transferred to nitrocellulose membrane, probed with different conjugates as indicated in FIGS. 25-27. Both the anti-full-length 6728 IgG-HRP and anti-6728C-IgG-HRP could differentiate the *T. canis* positive fecal sample from the nematode negative fecal samples (FIGS. 25 and 26). However, the anti-6728N IgG-HRP could not differentiate these two different fecal samples (FIG. 27). These data further confirmed that Copro6728 is about half the size of full-length DIV6728, in agreement with the data obtained from Mass spectrometry analysis and fecal ELISA.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

A number of examples to help illustrate the invention have been described. Nevertheless, it will be understood that various modifications may be made without departing from the spirit and scope of the invention. Accordingly, other embodiments are within the scope of the claims appended hereto.

What is claimed is:

1. A device for detecting the presence or absence of roundworm antigens from a sample; the device comprising a solid support, wherein the solid support has immobilized thereon one or more antibodies that are capable of specifically binding to a polypeptide that has an amino acid sequence that corresponds to SEQ ID NO:3, SEQ ID NO:4, SEQ ID NO:5, SEQ ID NO:6, SEQ ID NO:7, SEQ ID NO: 11, or Copro6728.

2. The device of claim 1 wherein the one or more antibodies are obtained by immunization with the polypeptide that has an amino acid sequence that corresponds to SEQ ID NO:3, SEQ ID NO:4, SEQ ID NO:5, SEQ ID NO:6, SEQ ID NO:7, SEQ ID NO: 11, or Copro6728.

3. The device of claim 1 wherein the sample is a fecal sample.

4. The device of claim 3 wherein the one or more antibodies do not specifically bind any coproantigen derived from the group consisting of hookworm, whipworm, and heartworm.

5. The device of claim 1 wherein one or more of the one or more antibodies are labeled.

6. The device of claim 1 wherein the device is an enzyme-linked immunosorbent assay device.

7. The device of claim 6 wherein the enzyme-linked immunosorbent assay device is a lateral flow immunoassay device.

8. The device of claim 1 wherein the sample is from a canine or a feline.

9. The device of claim 1 wherein the device further includes one or more reagents for the detection of one or more of the group consisting of: one or more non-roundworm parasites, one or more non-worm parasites, one or more viruses, one or more fungi, and one or more bacteria.

10. A kit for detection of one or more roundworm antigens in a mammalian sample, the kit comprising the device of claim 1, and one or more reagents sufficient for the detection of the one or more antigens.

11. The kit of claim 10 wherein the one or more reagents are selected from the group consisting of one or more indicator reagents, one or more antibody labeling compounds, one or more antibodies, one or more antigen capture reagents, one or more inhibitors, and one or more wash reagents.

* * * * *